United States Patent [19]

Schnitzer

[11] Patent Number: 5,914,127
[45] Date of Patent: Jun. 22, 1999

[54] ISOLATION AND USES OF CAVEOLAE

[75] Inventor: Jan E. Schnitzer, Encinitas, Calif.

[73] Assignee: Beth Israel Deaconess Medical Center, Boston, Mass.

[21] Appl. No.: 09/024,952

[22] Filed: Feb. 17, 1998

Related U.S. Application Data

[63] Continuation of application No. 08/582,917, Jan. 4, 1996, Pat. No. 5,776,770
[60] Provisional application No. 60/003,453, Sep. 8, 1995.
[51] Int. Cl.$^6$ .......................... A61K 9/127; A61K 31/00; C12N 11/02; C08G 18/00
[52] U.S. Cl. ...................... 424/450; 424/812; 435/317.1; 435/820; 521/154; 521/156; 514/2; 514/44; 530/300; 530/350
[58] Field of Search .................................. 424/450, 812; 435/317.1, 820; 521/154, 156; 530/300, 350; 514/2, 44

[56] References Cited

U.S. PATENT DOCUMENTS 5,281,700  1/1994  Schnitzer et al. ....................... 530/412

OTHER PUBLICATIONS

Anderson, R.G.W. et al., "Potocytosis: Sequestration and Transport of Small Molecules by Caveolae", *Science*, 255:410–411 (1992).
Anderson, R.G.W., "Caveolae: Where incoming and outgoing messengers meet", *Proc. Natl. Acad. Sci. USA*, 90:10909–10913 (1993).
Anderson, R.G.W., "Plasmalemmal caveolae and GPI–anchored membrane proteins", *Current Opinion in Cell Biology*, 5:647–652 (1993).
Brown, D.A. and Rose J.K., "Sorting of GPI–Anchored Proteins to Glycolipid–Enriched Membrane Subdomains during Transport to the Apical Cell Surface", *Cell*, 68:533–544 (1992).
Dupree, P. et al., "Caveolae and sorting in the trans–Golgi network of epithelial cells", *The EMBO J.*, 12(4):1597–1605 (1993).
Fra, A.M., "Detergent–insoluble Glycolipid Microdomains in Lymphocytes in the Absence of Caveolae", *J. of Biol. Chem.*, 269(49):30745–30748 (1994).
Gorodinsky, A. and Harris, D.A., "Glycolipid–anchored Proteins in Neuroblastoma Cells Form Detergent–resistant Complexes without Caveolin", *J. of Cell Biology*, 129(3):619–627 (1995).
Hannan, L.A. et al., "Correctly Sorted Molecules of a GPI–Anchored Protein Are Clusteered and Immobile When They Arrive at the Apical Surface of MDCK Cells", *J. of Cell Biol.*, 120(2):353–358 (1993).
Jacobson, B.S. et al., "Isolation and partial characterization of the luminal plasmalemma of microvascular endothelium from rat lungs", *European J. of Cell Biol.*, 58:296–306 (1992).

Lisanti, M.P. and Rodriquez–Boulan, E., "Polarized Sorting of GPI–Linked proteins in Epithelia and Membrane Microdomains", *Cell. Biol. International Reports*, 15(11):1023–1049 (1991).
Liasnti, M.P. et al., "Caveolin Forms a Hetero–Oligomeric Protein Complex That Interacts with an Apical GPI–linked Protein: Implications for the Biogenesis of Caveolae", *J. of Cell Biology*, 123(3):595–604 (1993).
Lisanti, M.P. et al., "Characterization of Caveolin–rich membrane Domains Isolated from an Endothelial–rich Source: Implications for Human Disease", *J. of Cell Biol.*, 126(1):111–126 (1994).
Lisanti, M.P. et al., "Caveolae, caveolin and caveolin–rich membrane domains: a signalling hypothesis", *Trends in Cell Biol.*, 4:231–235 (1994).
Mayor, S. et al., "Sequestration of GPI–Anchored Proteins in Caveolae Triggered by Cross–Linking", *Science*, 264:1948–1951 (1994).
Mescher, M.F., et al., "Actin–containing matrix associated with the plasma membrane of murine tumour and lymphoid cells", *Nature*, 289:139–144 (1981).
Peters, K.–R., et al., "Endothelial Plasmalemmal Vesicles Have a Characteristic Striped Bipolar Surface Structure", *J. of Cell Biol.*, 101:2233–2238 (1985).
Rothberg, K.G., et al., "Caveolin, a Protein Component of Caveolae Membrane Coats", *Cell*, 68:673–682 (1992).
Sargiacomo, M. et al., "Signal Transducing Molecules and Glycosyl–phosphatidylinositol–linked Proteins Form a Caveolin–rich Insoluble Complex in MDCK Cells", *J. of Cell Biol.*, 122(4):789–807 (1993).
Schnitzer, J.E. et al., "Preferential Interaction of Albumin–binding Proteins, gp30 and gp18, with Conformationally Modified Albumins", *J. of Biol. Chem.*, 267(34):24544–24553 (1992).

(List continued on next page.)

*Primary Examiner*—James Ketter
*Assistant Examiner*—William Sandals
*Attorney, Agent, or Firm*—Hamilton, Brook, Smith & Reynolds, P.C.

[57] ABSTRACT

Methods of isolating and purifying caveolae, microdomains of GPI-anchored proteins, and membranes consisting essentially of caveolae associated with microdomains of GPI-anchored proteins from endothelial cell membranes are disclosed. The methods comprise coating a luminal surface of an endothelial cell membrane with an adherent first ionic material by perfusion from a luminal cavity adjacent to the endothelial cell membrane, forming a pellicle by contacting the first ionic material with a second ionic material, and isolating and purifying the pellicle. The pellicle is then processed to isolate the desired cellular component. Caveolae which are substantially free of microdomains of GPI-anchored proteins; microdomains of GPI-anchored proteins which are substantially free of caveolae; and membranes consisting essentially of caveolae, microdomains of GPI-anchored proteins, and caveolae associated with microdomains of GPI-anchored proteins; all of which are substantially free of other cellular elements, are also disclosed.

14 Claims, 6 Drawing Sheets

OTHER PUBLICATIONS

Schnitzer, J.E. and Pinney, E., "Quantitation of specific binding of orosomucoid to cultured microvasculr endothelium: role in capillary permeability", *Am. Physiological Soc.*, H48–H55 (1992).

Schnitzer, J.E. and Oh, P., "Antibodies to SPARC inhibit albumin binding to SPARC, gp60, and microvascular endothelium", *Amer. Physiological Soc.*: H1872–H1879 (1992).

Schnitzer, J.E., "Update on the Cellular and Molecular Basis of Capillary Permeability", *Trends Cardiovas. Med.*, 3(4):124–130 (1993).

Schnitzer, J.E. and Bravo, J., "High Affinity binding, Endocytosis, and Degradation of Conformationally Modified Albumins", *J. of Biol. Chem.*, 268(10):7562–7570 (1993).

Schnitzer, J.E. et al., "Filipin–sensitive Caveolae–mediated Transport in Endothelium: Reduced Transcytosis, Scavenger Endocytosis, and Capillary Permeability of Select Macromolecules", *J. of Cell Biol.*, 127(5):1217–1232 (1994).

Schnitzer, J.E. et al., "Endothelial Caveolae Have the Molecular Transport Machinery for Vesicle Budding, Docking and Fusion Including VAMP, NSF, SNAP, Annexins, and GTPases", *J. of Biological Chem.*, 270(24):14399–14404 (1995).

Schnitzer, J.E. et al., "Caveolae from luminal plasmalemma of rat lung endothelium: Microdomains enriched in caveolin, $Ca^{2+}$–ATPase, and inositol triphosphate receptor", *Proc. Natl. Acad. Sci. USA*, 92:1759–1763 (1995).

Schnitzer, J.E. et al., "NEM inhibits transcytosis, endocytosis and capillary permeability: implication of caveolae fusion in endothelia", *Am. Physiological Soc.*, H48–H55 (1995).

Ying, Y.–S. et al., "Each Caveola Contains Multiple Glycosyl–phosphatidylinositol–anchored Membrane Proteins", *Cold Spring Harbor Symposia on Quantitative Biology*, LVII:593–604 (1992).

Zurzola, Chiara et al., "VIP21/caveolin, glycosphingolipid clusters and the sorting of glycosylphosphatidylinositol–anchored proteins in epithelial cells", *The EMBO J.*, 13(1):42–53 (1994).

Melkonian, K.A. et al., "Characterization of the proteins in a detergent–resistant membrane complex isolated from epithelial Cells", *Am. Soc. for Cell Biol., Thirty–fourth Ann. Mtg.*, 12/10–12/14 1994, S.F. CA (1994).

Fra, A.M. et al., "Detergent–insolubility of glycolipids and GPI–anchored proteins does not correlate with the presence of caveolae in lymphocytes", *Am. Soc. for Cell Biol., Thirty–fourth Ann. Mtg.*, 12/10–12/14 1994, S.F. CA (1994).

Chaney, L.K. and Jacobson, B.S., "Coating Cells with Colloidal Silica for High Yield Isolation of Plasma Membrane Sheets and Identification of Transmembrane Proteins", *Jour. of Biol. Chem.*, 258(16):10062–10072 (1983).

Glenney, J.R., Jr., "Tyrosine Phosphorylation of a 22–kDa Protein is Correlated with Transformation by Rous Sarcoma Virus", *Jour. of Biol. Chem.*, 264(34):20163–20166 (1989).

Glenney, J.R., Jr., "The sequence of human caveolin reveals identity with VIP21, a component of transport vesicles", *Fed. of European Biochem. Soc.*, 314(1):45–48 (1992).

Lisanti, M.P. et al., "Caveolae and human disease: functional roles in transcytosis, potocytosis, signalling and cell polarity", *Develop. Biol.*, 6:47–58 (1995).

Mason, P.W. and Jacobson, B.S., "Isolation of the dorsal, ventral and intracellular domains of HeLa cell plasma membranes following adhesion to a gelatin substrate", *Biochimica et Biophysica Acta.* 821(2):264–276 (1985).

Okada, S.S., et al., "Migrating Vascular Smooth Muscle Cells Polarize Cell Surface Urokinase Receptors after Injury in Vitro", *Experimental Cell Research* 217:180–187 (1995).

Schnitzer, J.E. et al., "Separation of Caveolae from Associated Microdomains of GPI–Anchored Proteins", *Science*, 269:1435–1439 (1985).

Fujimoto, T. et al., "Localization of Inositol 1,4,5–Trisphosphate Receptor–like Protein in Plasmalemmal Caveolae," *J. Cell Biol.* 119:1507–1513 (1992).

Lisanti, M.P. et al., "Characterization of Caveolin–rich Membrane Domains Isolated from an Endothelial–rich Source: Implications for Human Disease," *J. Cell Biol.* 126:111–126 (1994).

Stahl, A. and Mueller, B.M., "The Urokinase–Type Plasminogen Activator Receptor, a GPI–linked Protein, is Localized in Caveolae," *J. Cell Biol.* 129:335–344 (1995).

Ghitescu, L. et al., "Specific Binding Sites for Albumin Restricted to Plasmalemmal Vesicles of Continuous Capillary Endothelium: Receptor–mediated Transcytosis,"*J. Cell Biol.* 102:1304–1311 (1986).

Vasile, E. et al., "Visualization of the Binding, Endocytosis and Transcytosis of Low–Density Lipoprotein in the Arterial Endothelium In Situ," *J. Cell Biol.* 96:1677–1689 (1983).

ISOLATION AND USES OF CAVEOLAE

RELATED APPLICATION(S)

This application is a Continuation of application Ser. No. 08/582,917 filed Jan. 4, 1996 now U.S. Pat. No. 5,776,770 which claim the benefit of U.S. Provisional Application No. 60/003,453, entitled "Isolation and Uses of Caveolae" by Jan E. Schnitzer, filed Sep. 8, 1995. The teachings of these applications are incorporated herein by reference.

GOVERNMENT SUPPORT

Work described herein was supported in part by grants HL43278, HL522766, and IA33372 from the National Institutes of Health. The U.S. Government has certain rights in the invention.

BACKGROUND OF THE INVENTION

Cholesterol and glycolipids self-associate in lipid bilayers to form organized compositional microdomains (Thompson, T. E., et al., *Annu. Rev. Biophys. Chem.* 14:361 (1985)). Glycosyl-phosphatidylinositol (GPI)-anchored proteins and other lipid-linked proteins may preferentially partition into glycolipid microdomains that are resistant to nonionic detergent solubilization (Schroeder, R., et al., *Proc. Natl. Acad. Sci. USA.* 91:12130 (1994); Brown, D. A. and Rose, J. K., *Cell* 68:533 (1992); Letarte-Murhead, M., et al., *Biochem. J.* 143:51 (1974); Hoessli, D. and Runger-Brandle, E., *Exp. Cell. Res.* 166:239 (1985); Hooper, N. M. and Turner, A. J., *Biochem. J.* 250:865 (1968); Sargiacomo, M., et al., *J. Cell. Biol.* 122:789 (1993); Lisanti, M. P., et al., *J. Cell. Biol.* 123:595 (1993)). GPI-anchored proteins appear to be sorted into glycolipid, detergent-resistant "rafts" in the trans-Golgi network for polarized delivery to the cell surface by caveolin-rich smooth exocytotic carrier vesicles (Brown, D. A. and Rose, J. K., *Cell* 68:533 (1992); Sargiacomo, M., et al., *J. Cell. Biol.* 122:789 (1993); Lisanti, M. P., et al., *J. Cell. Biol.* 123:595 (1993); Brown, D., et al., *Science* 245:1499 (1989); Simons, K. and van Meer, G., *Biochemistry* 27:6197 (1988); Garcia, M., et al., *J. Cell Sci.* 104:1281 (1993); Kurzchalia, T. V., et al., *J. Cell Biol.* 118:1003 (1992); Dupree, P., et al., *EMBO J.* 12:1597 (1993); Hannan, L. A., et al., *J. Cell. Biol.* 120:353 (1993)). On the cell surface, they are thought to reside in smooth membrane invaginations known as caveolae (Rothberg, K. G., et al., *J. Cell. Biol.* 110:637 (1990); Ying, Y., et al., *Cold Spring Harbor Symp. Quant. Biol.* 57:593 (1992); Ryan, U. S., et al., *J. Appl. Physiol.* 53:914 (1982); Stahl, A. and Mueller, B. M., *J. Cell Biol.* 129:335 (1995)), which are apparently also rich in glycolipids, cholesterol, and caveolin (Kurzchalia, T. V., et al., *J. Cell Biol.* 118:1003 (1992); Dupree, P., et al., *EMBO J.* 12:1597 (1993); Parton, R. G., *J. Histochem. Cytochem.* 42:155 (1994); Rothberg, K. G., et al., *Cell* 68:673 (1992); Schnitzer, J. E., et al., *Proc. Natl. Acad. Sci. USA* 92:1759 (1995); Montessano, R., et al., *Nature* 296:651 (1982)). Antibody cross-linking of cell surface glycolipids (Thompson, T. E., et al., *Annu. Rev. Biophys. Chem.* 14:361 (1985)) and GPI-linked proteins (Mayor, S., et al., *Science* 264:1948 (1994)) can increase sequestration into clusters and induce cell activation (Thompson, T. E., et al., *Annu. Rev. Biophys. Chem.* 14:361 (1985); Thompson, L. F., et al., *J. Immunol.* 143:1815 (1969); Korty, P. E., et al., *J. Immunol.* 146:4092 (1991); Davies, L. S., *J. Immunol.* 141:2246 (1988)), apparently through lipid-anchored nonreceptor tyrosine kinases (NRTKs) (Stefanova, I., et al., *Science* 245:1016 (1991); Shenoy-Scaria, A. M., et al., *J. Immunol.* 149:3535 (1992); Thomas, P. M. and Samelson, L. E., *J. Biol. Chem.* 267:12317 (1992); Cinek, T. and Horejsi, V., *J. Immunol.* 149:2262 (1992)). Caveolae have been implicated not only in signaling but also in transport via endocytosis, transcytosis, and potocytosis (Montessano, R., et al., *Nature* 296:651 (1982); Schnitzer, J. E., *Trends Cardiovasc. Med.* 3:124 (1993); Oh, P., et al., *J. Cell Biol.* 127:1217 (1994); Schnitzer and Oh, P., *J. Biol. Chem.* 269:6072 (1994); Millci, A. J., et al., *J. Cell Biol.* 105:2603 (1987); Anderson, R. G. W., et al., *Science* 265:410 (1992)). Low density, Tritoninsoluble membranes are frequently equated with caveolae (Sargiacomo, M., et al., *J. Cell. Biol.* 122:789 (1993); Lisanti, M. P., et al., *J. Cell. Biol.* 123:595 (1993); Chang, W. J., et al., *J. Cell. Biol.* 126:127 (1994); Lisanti, M. P., et al., *J. Cell. Biol.* 126:111 (1994)). The physiological functions of, and interrelations between, caveolae, detergent-resistant microdomains, and various lipid-anchored molecules remain undefined.

SUMMARY OF THE INVENTION

The present invention relates to methods of isolating and purifying microdomains or components of the cell surface or plasma membrane; the resulting purified microdomains and components (e.g., proteins, peptides, lipids, glycolipids) and uses therefor. In one embodiment, the present invention relates to methods of purifying microdomains of plasma membranes, including caveolae, microdomains of GPI-anchored proteins (G-domains) and membrane fragments consisting essentially of caveolae and G domains; the resulting purified microdomains and uses therefor. In a second embodiment, the present invention relates to methods of purifying detergent-sensitive (detergent-soluble) microdomains and cytoskeletal components; the resulting purified microdomains and uses for these components.

Plasma membrane components purified by methods of the present invention are useful, directly or indirectly, in the transport of molecules, such as drugs, DNA molecules, or antibodies in various cells (e.g., epithelial, endothelial, fat cells). For example, such agents targeted to caveolae in endothelium will be transported by the caveolae into and/or across the endothelium, and, thus, are useful in breaking through a critical barrier which prevents entry of many molecules, including drugs, into most tissues from the circulating blood. Caveolae and other plasma membrane components identified as described herein can be used to identify mechanisms or routes by which molecules can be delivered into cells, particularly endothelial cells, through the action of caveolae, G domains and other plasma membrane domains and components. For example, molecules residing in caveolae can be targeted by antibodies or natural ligands to caveolar proteins or receptors such as the insulin receptor, thereby bringing agents conjugated to the antibody or ligand into and/or across the endothelium. Alternatively, purified caveolae can be modified to serve as drug delivery vehicles, such as by introducing into them an agent, such as a drug, including a peptide or small organic molecule; a gene encoding a therapeutic or diagnostic peptide/protein; or an antibody. The resulting modified purified caveolae can be introduced into an individual, in whom they act to deliver the agent.

In the present method, plasma membranes are purified from a cell type of interest, such as endothelial cells, using a method such as that described in U.S. Pat. No. 5,281,700 and Schnitzer, J. E. et al., *Proc. Natl. Acad. Sci.*, USA, 92:1759–1763 (1995); the teachings of both of these documents are incorporated herein by reference. The purified plasma membranes are then subfractionated into specific components or microdomains. Plasma membrane microdomains include caveolae, microdomains of GPI-anchored proteins (G-domains) and plasma membrane microdomains consisting essentially of caveolae, G domains and caveolae associated with G domains. Other microdomains include detergent-soluble domains and domains comprising cytoskeletal components.

In the method of the present invention, a cell plasma membrane, such as an endothelial cell plasma membrane, is specifically marked by altering a physical characteristic, such as by increasing its density; the change in physical characteristic of the membrane, such as increased density, is used as the basis for separating the plasma membrane from the other cell components (i.e., purifying the plasma membranes). In one embodiment, the present method of purifying caveolae or G domains entails silica coating of plasma membranes and comprises two broad phases: purification of cell plasma membranes and purification of subfractions or microdomains of the plasma membranes.

The purified cell plasma membranes are subfractionated and the desired membrane component or microdomain is isolated from the appropriate subfraction, resulting in isolation of the purified plasma membrane microdomain or components. In this embodiment, the luminal endothelial cell plasma membranes (normally exposed to the circulating blood) are coated with a suspension of cationic colloidal silica particles, such as by in situ perfusion of lung vasculature. This coating procedure forms a stable membrane pellicle (for example, attached to the luminal endothelial cell surface) which, after tissue disruption (e.g., by homogenization), results in silica-coated membrane sheets which are separated from the remaining cell fragments or components based on density differences (e.g., by centrifugation), resulting in production of silica-coated plasma membrane pellets (in this case, silica-coated luminal endothelial cell plasma membrane pellets). By both biochemical and morphological criteria, these pellets represent purified plasma membranes with caveolae still attached and litle, if any, contamination from other sources.

Purified, silica-coated endothelial plasma membranes are processed, according to the appropriate embodiment of the present method, to isolate the desired plasma membrane microdomain, such as caveolae and/or microdomains of GPI-anchored proteins (G domains).

Caveolae, which are on the cytoplasmic side of the plasma membrane, (opposite to the silica coating in the silica-coated membrane pellets) are isolated as follows: silica-coated membrane pellets are subjected to a membrane disruption technique, such as shearing or sonication, to strip off the caveolae from the stabilized silica-coated membrane pellet. For example, membrane disruption causing selective removal of caveolae from silica-coated plasma membrane is carried out by shearing during homogenization and can occur in the presence or absence of detergent. Caveolae are purified from the remaining silica-coated membranes on the basis of density, such as by sucrose density gradient centrifugation. The resulting purified caveolae are essentially free of GPI-anchored proteins and represent purified caveolae by morphological and biological criteria.

G-domains are isolated separately from caveolae by the method of the present invention by subjecting silica-coated plasma membranes already stripped of caveolae to a high salt concentration, of approximately 1.0 molar. This results in reduced electrostatic interactions between the cationic silica particles and the polyanionic plasma membrane and, as a result, causes separation of the plasma membrane from the silica coating. This material (the plasma membrane no longer adherent to the silica coated pellicle) is homogenized in the presence of an appropriate detergent (e.g., TRITON X-100). Membrane disruption occurs at an appropriate temperature, which is generally from about 4° C. to about 8° C. Low temperature is necessary primarily if detergent is used, because caveolae are detergent-resistant only at low temperatures. The membrane fraction containing G-domains is isolated (purified from other homogenate components) on the basis of density, such as by sucrose density gradient centrifugation. The resulting purified G domains are rich in GPI-anchored proteins and essentially free of caveolae and caveolae markers.

Plasma membrane microdomains consisting essentially of caveolae and G domains together are isolated by the method of the present invention by isolating the silica-coated plasma membrane pellets. The silica-coated plasma membrane pellets with attached caveolae are subjected to a high salt concentration, as described above, to separate the plasma membrane from the silica coating. The separated plasma membrane is homogenized in the presence of an appropriate detergent (e.g., TRITON X-100) and low-density, detergent-resistant membrane domains are separated on the basis of density, such as by sucrose density gradient centrifugation and purified. These membrane domains consist essentially of caveolae, G domains and caveolae associated with G domains.

The invention further relates to purified caveolae, which are substantially free of other plasma membrane components; purified microdomains of GPI-anchored proteins (purified G domains) which are substantially free of other membrane components; and membrane domains consisting essentially of caveolae associated with microdomains of GPI-anchored proteins, which are substantially free of other plasma membrane components.

The purified caveolae, G domains, and co-isolated caveolae and G domains are useful for the identification of molecules and proteins which are involved in intra- or trans-cellular transport and cell surface signal transduction and communication. They thus make it possible to identify new means by which molecules can be delivered to plasma membranes and, if desired, enter the cell, cross from one side of the cell to the other, or provide a signal to the cell that alters its function. For example, one way the purified caveolae and the purified G domains can be used is to make specific probes or antibodies. Such antibodies can be used as vectors to target the caveolae or G domains and to influence the transport of molecules across the plasma membrane. Such vectors can be used to deliver agents into and/or across the cell, such as drugs, genes, or antibodies and particularly to deliver agents into and/or across the endothelium. In addition, the purified caveolae and the G domains of the current invention can be used to deliver agents into and/or across the cell, such as drugs, genes, or antibodies and particularly to deliver agents into and/or across the endothelium. In addition, these domains can be used as transfer vehicles. For example, lipid-anchored molecules added to or naturally found in the purified caveolae or purified G domains can also, upon introduction into the peripheral blood circulation, interact with blood vessel endothelium, and be transferred to that endothelium, including directly into the plasma membrane.

BRIEF DESCRIPTION OF THE DRAWINGS

FIG. 5A depicts differential detergent extraction performed on silica-coated endothelial cell membranes (P). FIG. 5B demonstrates co-isolation of caveolin and 5'-NT in detergent-resistant membranes derived without silica coating. FIG. 5C demonstrates lack of GPI-anchored proteins in the purified caveolae enriched in caveolin and ganglioside $GM_1$. FIG. 5D demonstrates separate isolation of the GPI-anchored protein microdomain from the silica-coated membranes. FIG.5E demonstrates immunoblot analysis of caveolae isolated without Triton X-100.

DETAILED DESCRIPTION OF THE INVENTION

The present invention relates to purified plasma membrane microdomains and components; methods of producing the purified plasma membrane microdomains and components; and uses for these purified plasma membrane microdomains and components, including identifying molecules involved in intra- or trans-cellular transport or cell surface signal transduction and communication and targeting of the endothelium (e.g., for delivery of an agent or for gene therapy). The present method can be carried out on any cell type (e.g., endothelial, epithelial, and fat cells) whose plasma membrane contains the desired component. Components which can be isolated by the present method include caveolae, G domains, membrane fragments consisting essentially of caveolae associated with G domains, detergent soluble components, and cytoskeletal components.

Figure 1:
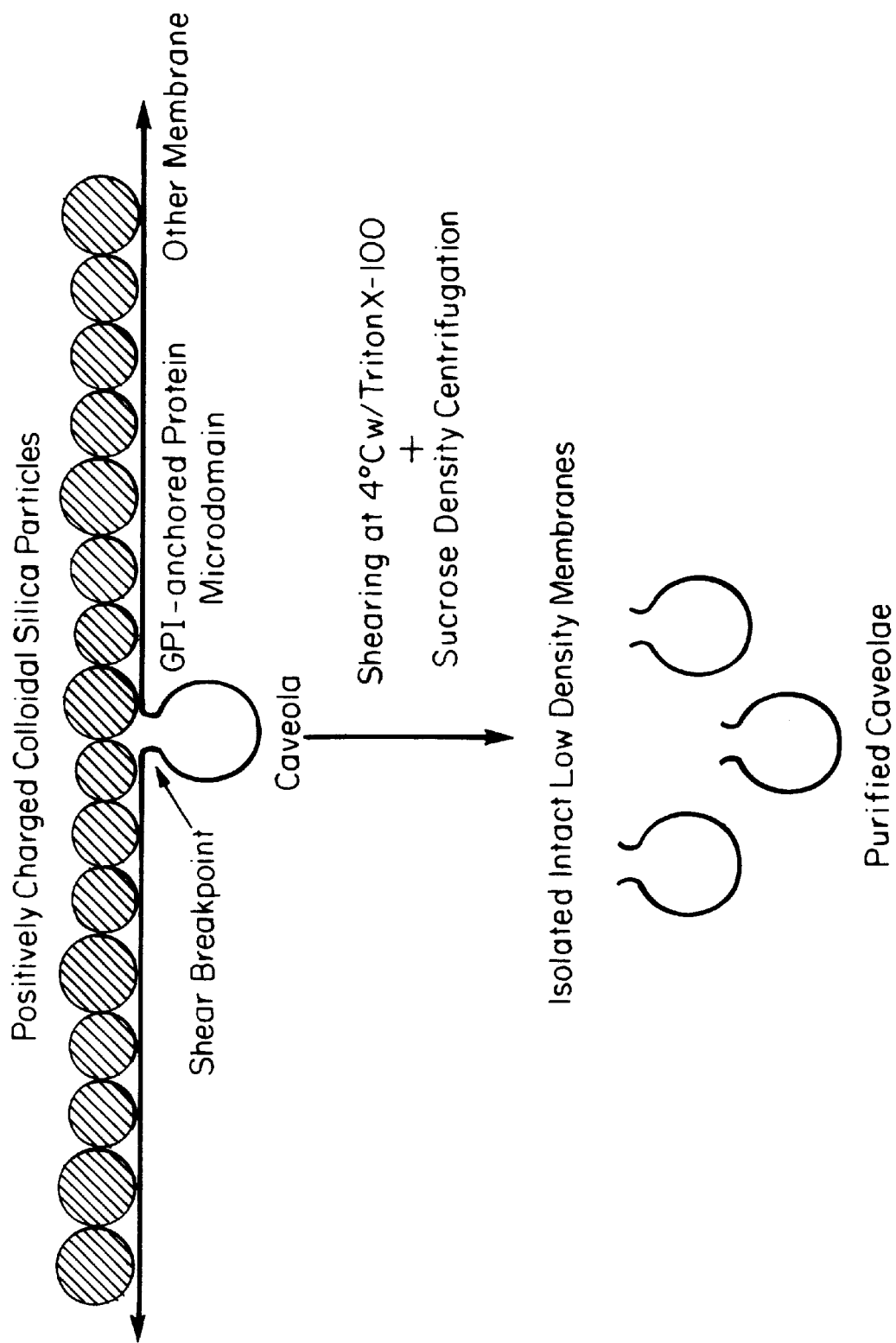
FIG. 1 is a schematic representation of isolation of highly purified plasma membrane caveolae.

In one embodiment, the present invention relates to caveolae purified from plasma membranes, such as endothelial cell plasma membranes, by the method described herein. As described in detail in Examples 1 and 2 and represented schematically in FIG. 1, highly purified caveolae are obtained from isolated luminal endothelial cell plasma membranes. The caveolae of the invention are purified based on both morphological and biochemical criteria. They are substantially free of microdomains of GPI-anchored proteins, GPI-anchored proteins and Rab5 (a guanosine triphosphate (GTP)-binding protein that is found in detergent-resistant complexes, as described below). By electron microscopy, this fraction contains a rather homogeneous population of vesicles predominantly <1000Å in diameter, and have a morphologically distinctive appearance of caveolae (Schnitzer, J. E., et al., Proc. Natl. Acad. Sci. USA 92:1759 (1995)). Purified caveolae have been obtained by coating the surface of cells (such as endothelial cells) with cationic colloidal silica particles; separating the silica-coated cell plasma membranes from the remainder of the cell and any associated tissue, to produce silica-coated cell plasma membranes; stripping the caveolae (present on the side of the membrane opposite that to which the silica particles attached) from the membrane by a membrane disruption technique (such as shearing or sonication); and separating the caveolae from the other plasma membrane components (which include the remaining silica-coated plasma membranes rich in GPI-anchored proteins but devoid of caveolae and caveolin). This separation is carried out on the basis of density, such as by sucrose density gel centrifugation. In one embodiment, endothelial cell plasma membranes are subjected to shearing in the presence of a detergent (e.g., TRITON X-100) during homogenization at an appropriate temperature (e.g., approximately 4° C.–8° C.). Low temperature is necessary if detergent is used, because caveolae are only detergent-resistant at low temperatures. At physiologic temperature (37°C.), caveolae are solubilized by detergent. Detergent appears to facilitate the removal of caveolae from their attachment point on the plasma membrane, and thus facilitate the stripping process, but is not essential or necessary for the process. In a second embodiment, endothelial cell plasma membranes are subjected to shearing during homogenization in the absence of detergent.

In either embodiment, the result is separation of caveolae from other cell membrane components and isolation of purified caveolae. Characterization of the purified caveolae showed that they are very enriched in caveolin; the glycolipid $GM_1$; the plasmalemmal $Ca^{2+}$-dependent adenosine triphosphatase; and the inositol 1,4,5-triphosphate receptor. These four molecules have all been shown by independent means (localization by electron microscopy) to reside on the cell surface almost exclusively in caveolae (Dupree, P., et al., EMBO J. 12:1597 (1993); Parton, R. G., J. Histochem. Cytochem. 42:155 (1994); Rothberg, K. G., et al., Cell 68:673 (1992); Montessano, R., et al., Nature 296:651 (1982); Fujimoto, T., et al., J. Cell. Biol. 119:1507 (1992); Fujimoto, T., J. Cell. Biol. 120:1147 (1993)) and thus represent key markers of the caveolae. These four caveolar markers which are all present amply in the silica-coated plasma membrane pellet, fractionate almost totally into the purified caveolae. Little if any remains in the other membrane fractions. In contrast, angiotensin-converting enzyme, band 4.1 and β-actin, which were all present amply in the silica-coated plasma membrane fraction (P) are almost totally excluded from the purified caveolae.

Figure 2:
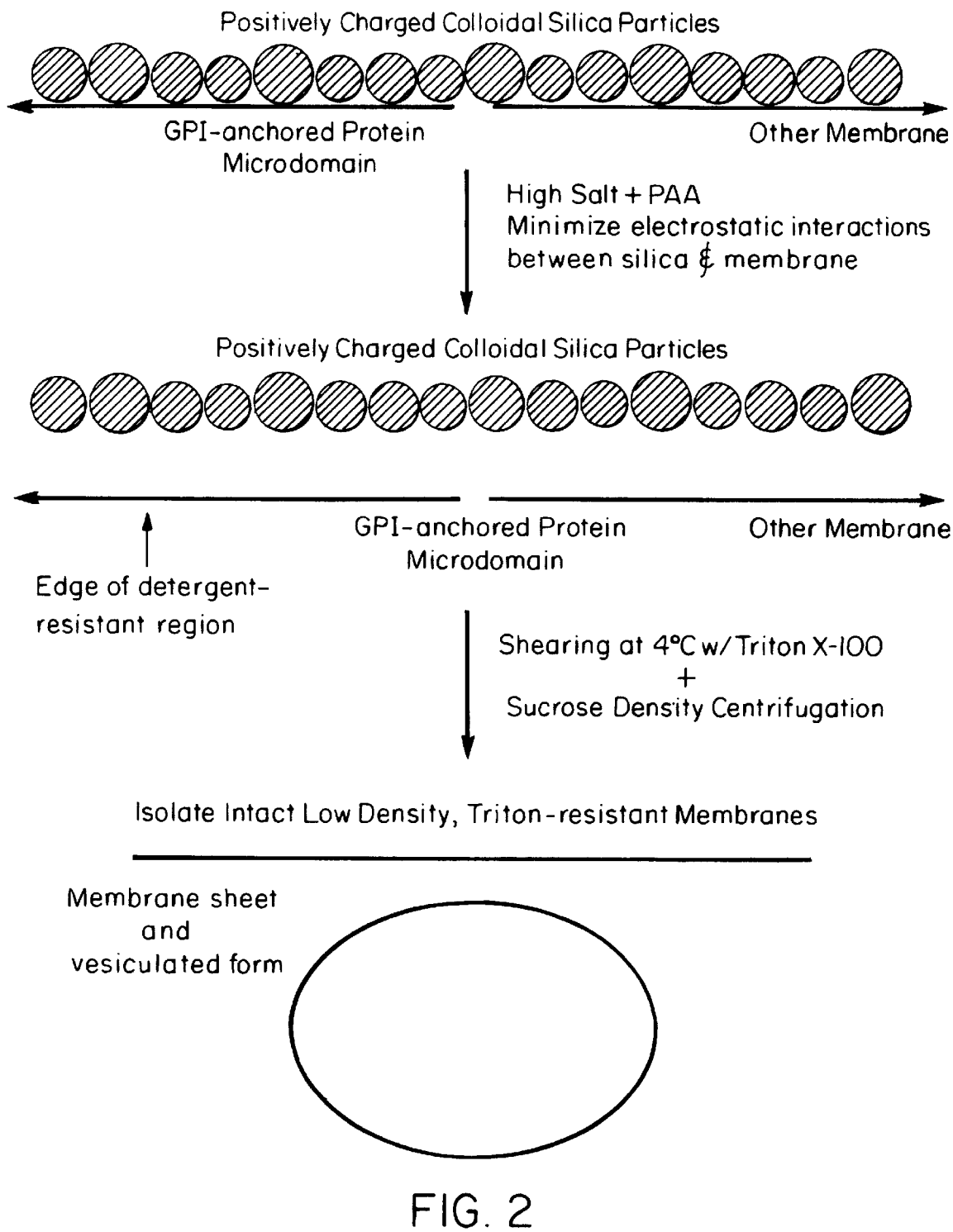
FIG. 2 is a schematic representation of isolation of GPI-anchored protein microdomains from plasma membranes.

In a further embodiment, the present invention relates to microdomains of GPI-anchored proteins (G domains) purified from plasma membranes, such as endothelial cell plasma membranes. The microdomains of GPI-anchored proteins are purified, in that they are substantially free of caveolae, caveolin and $GM_1$ (a lipid-anchored, cholera toxin-binding ganglioside $GM_1$ that has been localized with gold labeling inside the caveolae, as described below). As described in Example 3 and represented schematically in FIG. 2, G domains were isolated from cell plasma membranes (e.g., endothelial plasma membranes) originally isolated from the cells (e.g., by use of silica coating, as described in Example 1) and stripped of caveolae. The isolated silica-coated plasma membranes stripped of caveolae were subjected to a salt concentration sufficiently high to reduce/minimize electrostatic interactions between the silica particles and plasma membrane, resulting in separation of the plasma membranes from the particles. The resulting non-coated plasma membranes (previously stripped of caveolae) were subjected to a membrane disruption technique (e.g., shearing) in the presence of a detergent (e.g., TRITON X-100) and then subjected to a separation technique which separates components based on density (e.g., sucrose density centrifugation), resulting in isolation of intact G domains, which are low density, detergent-insoluble (resistant) membrane microdomains; are rich in GPI-anchored proteins; and are substantially free of caveolae.

The data herein indicate that GPI-anchored proteins partition into diffusion-restrictive microdomains, some of which may associate with caveolae as an annular region at the opening or neck of the caveolae. Because both caveolae and G domains are resistant to detergent solubilization, the normally flat membrane region surrounding the opening of the caveolea has been excised from the plasmalemma to form an intact large vesicle with a caveolea still attached and located usually inside but sometimes outside of the vesicle upon detergent extraction. The silica coating prevents the co-isolation of this microdomain with the caveolae, and allows separate isolation of caveolae and the G domain.

In another embodiment, the present invention relates to plasma membrane domains which consist essentially of caveolae, G domains (some of which are associated with each other) and are purified, for example, from endothelial cell plasma membranes. The term, "associated with," as used herein, indicates that some of the caveolae are attached to the G domains, rather than being separated. As described in Example 4, and represented schematically in FIG. 3, plasma membrane domains consisting essentially of caveolae, G domains, and caveolae associated with G domains are produced by isolating silica-coated cell membranes with caveolae still attached, as described above; subjecting the silica-coated cell plasma membranes to high salt to separate the silica coating from the membranes, and subjecting the membranes to a membrane disruption technique, such as shearing or sonication, in the presence of an appropriate detergent, such as TRITON X-100. This results in separation of the membrane into various components, including caveolae associated with G domains. Domains consisting essentially of caveolae, G domains, together with caveolae associated with G domains are detergent resistant, and can be separated from other components on the basis of density, such as by sucrose density centrifugation.

In another embodiment, other components of the cell plasma membrane can be isolated. Such components include detergent-soluble components or cytoskeletal components which remain after isolation of caveolae, G domains, or caveolae associated with G domains, as described above. These other components are substantially free of caveolae and/or G domains. For example, after isolation of G domains that are substantially free of caveolae, as described above, the remaining detergent-soluble components can be isolated and purified.

As a result of these discoveries, methods are now available to isolate caveolae that are substantially free of microdomains of GPI-anchored proteins and other cell components; G domains that are substantially free of caveolae and other cell components; and co-isolated plasma membrane microdomains that consist essentially of caveolae, G domains and caveolae associated with G domains. The caveolae, G domains, and/or co-isolated plasma membrane microdomains can be isolated from any endothelial cell plasma membrane from any tissue. Tissues from which endothelial cell membrane can be used include vascular, pulmonary, cardiac, cerebral, nephric, hepatic and endocrinous tissue, including the vascular system, lung, heart, liver, kidney, brain and other organs. For example, caveolae, G domains and/or co-isolated plasma membrane domains can be isolated from vascular endothelium by perfusion through the blood vessels, or intestinal epithelium by perfusion through the intestine. In addition, caveolae, G domains and/or co-isolated plasma membrane domains can also be isolated from a variety of cells, such as those grown in cultures.

In a specific embodiment of the invention, specific microdomains are isolated from endothelial cell plasma membranes by first isolating cell membranes, by forming a coating of an adherent, first ionic material on a luminal surface of the endothelial cell membrane by perfusing the ionic material into a luminal cavity adjacent to the endothelial cell membrane; crosslinking the coating to form a pellicle adherent to the endothelial membrane (referred to as a pellicle-endothelial membrane complex) by contacting the luminal surface of the ionic material coating with an oppositely charged ionic material reactive with the first ionic material; and separating the complex from other tissue elements by a method based on differences in size or density (e.g., by centrifugation), thus producing coated membrane pellets. Subsequently, specific microdomains can be isolated. For example, caveolae can be isolated by stripping caveolae from the coated membranes by shearing during homogenization, in the presence or absence of detergent; and isolating the caveolae from other components on the basis of density, such as by sucrose density gradient centrifugation. Caveolae isolated by this method are substantially free of G domains. Alternatively, G domains can be isolated by isolating the coated membranes after isolating and removing the caveolae; subjecting the coated membranes to high salt to remove the silica coating; and isolating the membranes. These membranes isolated by this method consist essentially of G domains.

In the preferred embodiments of the invention, the first ionic material is colloidal silica and the second ionic material is an acrylic polymer. One of many alternatives is to use magnetic particles to coat the membranes, which can subsequently be isolated, using standard magnetic techniques.

The purified caveolae, the purified microdomains of GPI-anchored proteins, and the purified co-isolated plasma microdomains comprising caveolae associated with G domains are useful for the identification of molecules and proteins which are involved in intra- or trans-cellular transport. Furthermore, the caveolae and the G domains are purified and, thus, can be used to distinguish and identify proteins which are limited to either the caveolae or the microdomains, but are not present in both. For example, purified caveolae can be used to generate antibodies, either monoclonal or polyclonal, using standard techniques. The term "antibody", as used herein, encompasses both polyclonal and monoclonal antibodies, as well as mixtures of more than one antibody reactive with caveolae (e.g., a cocktail of different types of monoclonal antibodies reactive with the caveolae). The term antibody is further intended to encompass whole antibodies and/or biologically functional fragments thereof, chimeric antibodies comprising portions from more than one species, humanized antibodies and bifunctional antibodies. Biologically functional antibody fragments which can be used are those fragments sufficient for binding of the antibody fragment to purified caveolae. Once the antibodies are raised, they are assessed for the ability to bind to purified caveolae. Conventional methods can be used to perform this assessment.

The chimeric antibodies can comprise portions derived from two different species (e.g., a constant region from one species and variable or binding regions from another species). The portions derived from two different species can be joined together chemically by conventional techniques or can be prepared as single contiguous proteins using genetic engineering techniques. DNA encoding the proteins of both the light chain and heavy chain portions of the chimeric antibody can be expressed as contiguous proteins.

Monoclonal antibodies (mAb) reactive with purified caveolae can be produced using a variety of techniques, such as somatic cell hybridization techniques (Kohler and Milstein, *Nature* 256: 495–497 (1975)), in situ techniques and phage library methods. For example, purified caveolae can be used as the immunogen. Alternatively, synthetic peptides corresponding to portions of proteins found in the caveolae can be used as immunogens. An animal is immunized with such an immunogen to obtain antibody-producing spleen cells. The species of animal immunized will vary depending on the specificity of mAb desired. The antibody producing cell is fused with an immortalizing cell (e.g., a myeloma cell) to create a hybridoma capable of secreting antibodies. The unfused residual antibody-producing cells and immortalizing cells are eliminated. Hybridomas producing desired antibodies are selected using conventional techniques and the selected hybridomas are cloned and cultured.

Polyclonal antibodies can be prepared by immunizing an animal in a similar fashion as described above for the production of monoclonal antibodies. The animal is maintained under conditions whereby antibodies reactive with purified caveolae are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG, IgM).

Alternatively, purified G domains or purified silica-coated membranes can be used to generate antibodies, as can any membrane fraction obtained as described herein. Synthetic peptides corresponding to portions of proteins from any of the fractions can also be used. Purified caveolae can be used to identify those antibodies which bind caveolae. Alternatively, purified G domains can be used to identify those antibodies which bind G domains.

Antibodies as described above can be used to identify further the proteins associated with intra- and trans-cellular transport: for example, the antibodies can be applied to endothelium in order to determine whether they interfere with transport in endothelium. Antibodies can additionally be used as vectors to deliver agents into and/or across the endothelium.

The purified caveolae or G domains of the current invention can be used to target the endothelium, such as for delivery of an agent or for gene therapy. Agents which target caveolae or the G domains may be more easily delivered to the cell and, if desired, enter the cell, cross from one side of the cell to the other, or provide a signal to the cell that alters its function. For example, agents such as antibodies, drugs, or other molecules which bind to G domains or to proteins in caveolae (e.g., the insulin receptors) target the caveolae or the G domains and may thereby be moved into and/or across the epithelium. Such antibodies, drugs, or other molecules can also be used as transport agents, by conjugating another agent (such as a drug or a gene) to the agent which targets the caveolae or G domain. In this manner, the purified caveolae and the purified microdomains of GPI-anchored proteins are also useful as transport vehicles, to move agents across the endothelial layer. The physical association of G domains with caveolae suggests functional interplay between them; therefore, these structures may provide a platform for ligand processing by integrating signal transduction with membrane transport. Binding of natural ligands or antibodies to GPI-linked proteins can induce clustering (Schroeder, R., et al., *Proc. Natl. Acad. Sci.* USA. 91:12130 (1994); Mayor, S., et al., *Science* 264:1948 (1994)), internalization by caveolae via potocytosis (Anderson, R. G. W., et al., *Science* 255:410 (1992); Rothberg, G., et al., *J. Cell.*

*Biol.* 111:2931 (1990)) or endocytosis (Keller, E.-A., et al., *EMBO J.*, 3:863 (1992); Bamezai, A., et al., *Eur. J. Immunol.* 22:15 (1992); Parton, R. G., et al., *J. Cell. Biol.* 127:1199 (1994)), and even cell activation (Thompson, L. F., et al., *J. Immunol.* 143:1815 (1989); Korty, P. E., et al., *J. Immunol.* 146:4092 (1991); Davies, L. S., *J. Immunol.* 141:2246 (1988)). Signaling may regulate caveolar processing (Parton, R. G., et al., *J. Cell Biol.* 127:1199 (1994); Smart, E. J., et al., *J. Cell. Biol.* 124:307 (1994)), and various mediators of signaling may reside in caveolae (Schnitzer, J. E. et al., *Proc. Natl. Acad. Sci., USA* 92:1759 (1995); Fujimoto, T., et al., *J. Cell. Biol.* 119:1507 (1992); Fujimoto, T., *J. Cell. Biol.* 120:1147 (1993); Schnitzer, J. E., et al., *J. Biol. Chem.* 270:14399 (1995)). Lastly, surface-bound molecules are endocytosed or transcytosed by caveolae in endothelium (Montessano, R., et al., *Nature* 296:651 (1982); Schnitzer, J. E., *Trends Cardiovasc. Med.* 3:124 (1993); Oh, P., et al., *J. Cell Biol.* 127:1217 (1994); Schnitzer and Oh, P., *J. Biol. Chem.* 269:6072 (1994); Millci, A. J., et al., *J. Cell Biol.* 105:2603 (1987); Schnitzer, J. E., et al., *J. Biol. Chem.* 264:24544 (1992); Schnitzer, J. E., and Bravo, J., *J. Biol. Chem.* 268:7562 (1993)). Disassembly of caveolae prevents such transport (Oh, P., et al., *J. Cell Biol.* 127:1217 (1994)), and molecular mapping of purified caveolae reveals the presence of SNARE fusion proteins and guanosine triphosphatases necessary for regulated N-ethylmaleimide-sensitive vesicular transport (Schnitzer, J. E., et al., *J. Biol. Chem.* 270:14399 (1995); Schnitzer, J. E., et al., *Am. J. Physiol.* 37:1148 (1995)). Thus, as a result of the purification of the endothelial caveolae as described herein, it has become apparent that caveolae are indeed vesicular carriers and contain the molecular machinery for integrating signaling with carrier transport. Dynamic ligand processing via clustering, signaling, and vesicular transport may occur through the association of the GPI-linked protein microdomains with caveolae or even possibly via caveolar formation. Such specialized distinct microdomains may exist separately or associated with each other not only to organize signalling molecules but also to process surface-bound ligands differentially.

Thus, caveolae (and associated membrane components, such as GPI-anchored proteins) play a key role in the transport of molecules into and across many types of cell membranes and particularly are involved in transporting molecules into and/or across the endothelium and, as a result, across the endothelial barrier. This is of considerable interest and value because of the role the endothelium plays in many tissues in the body as a barrier to passage of substances, such as drugs and other agents which can have a beneficial effect if they are made available to the underlying tissue. Work described herein makes it possible to identify means by which transport across cell membranes, particularly endothelial cell membranes, can be facilitated and, if desired, effected in a tissue specific manner (i.e., directed to a selected tissue type or types through caveolae and/or GPI-anchored proteins which are cell-type specific). In addition to mediating, controlling, and/or regulating the transport of various molecules including ions, small molecules, proteins, and even water into cells, such as endothelial cells, caveolae have a role in cell surface signal transduction and communication. Recent work has shown that caveolae may also act in interactions between cells and surrounding tissues and fluids and that in doing so, they store and process messenger molecules (e.g., CAMP, Calcium) and initiate phosphorylation cascades by using kinases such as non-receptor tyrosine kinases. (See, e.g., Anderson, R. G. W., *Proc. Natl. Acad. Sci. USA*, 90:10909–10913 (1993);

Anderson, R. G. W., *Current Opinion in Cell Biology* 5:647–652 (1993)).

As a result, the availability of purified caveolae, G domains and membrane domains consisting essentially of caveolae and G domains makes it possible to deliver molecules, such as drugs and diagnostic agents, to and/or across cell membranes, such as endothelial cell membranes, and to alter cell signaling and communication, such as by interacting with molecules shown to be present in or associated with caveolae and/or G domains and to have a role in signal transduction and communication. For example, purified caveolae of the present invention have been characterized as to constituent proteins and other components and can be further assessed to identify components which play key roles in transport or signal transduction and communication, either in a variety of cell types (to permit a general effect on cells) or in a specific cell type (to permit a selective effect). For example, plasma membrane components can be identified which improve transport of a drug such as an immunotoxin (to be delivered to a tumor or other malignancy) for cancer therapy or a selective stimulant (to be delivered to heart tissue and, more specifically cross the heart endothelial barrier to the underlying and normally less accessible cardiomyocytes) for treatment of cardiac conditions. Alternatively, plasma membrane components can be identified which will facilitate gene delivery into cells, such as epithelial cells, in which the gene will be processed to produce a therapeutic or diagnostic protein or peptide or an antisense nucleic acid. For example, if the goal is to introduce a gene into blood vessels in order to produce and secrete an anticoagulant or blood thinning protein, the appropriate target will be the endothelium, especially in heart tissue. Caveolae and/or GPI-anchored proteins present in (and possibly unique to) endothelial cell plasma membranes in heart/and/or blood vessels can be identified, using purified caveolae and/or G domains described herein; and used to target or direct a gene delivery vehicle (such as a plasmid or viral vector, or protein- or peptide-DNA conjugate) to heart tissue and/or blood vessels. Similarly, lipid-anchored proteins found in caveolae or G domains can be introduced into the peripheral blood circulation, where they interact with the epithelium of the blood vessels and can be transferred to the blood vessel epithelium.

Directing delivery of a drug or other agent which is to enter a cell through the action of caveolae, GPI-anchored proteins or other plasma membrane domain can be carried out by using as a "probe" or transporting molecule a molecule (such as an antibody, a peptide, a virus, a ligand) which has a relatively high affinity interaction with a component of caveolae, G domains or other plasma membrane domain. The probe or transporting molecule can itself be the drug or agent whose entry into cells, such as endothelial cells, is desired or can be attached to a second molecule whose entry into cells is desired. The transporting molecule and the attached molecule will be extracted from the blood and accumulated in the targeted tissue by action of the caveolae. For example, an antibody or other molecule which recognizes a protein found only in lung caveolae can be used to direct a drug, which can be the antibody or other molecule or can be delivered by their action, to lung tissue for therapeutic or diagnostic purposes. The drug will be accumulated in the lung tissue via lung caveolae and, thus, made available to the tissue for the desired effect. Similarly, such probes or transporting molecules (which target caveolae in a specific tissue type or generally bind caveolae on many tissue types) can be used to introduce drugs or other agents into a variety of tissue types.

Proteins and other components of caveolae or G domains which can be targets for the probes or transporting molecules can be identified using purified caveolae or G domains of the present invention. Conversely, probes or transporting molecules can also be identified using purified caveolae or G domains described herein. To identify such molecules, standard assays can be used, including: two-dimensional gel analysis followed by microsequencing, Western blotting with antibodies to known proteins (as described herein), or blotting with antibodies as described above.

It is also possible to use purified caveolae, G domains and membrane fragments consisting essentially of caveolae and G domains as delivery vehicles. For example, purified caveolae can be modified to contain a drug or other agent (such as a chemotherapeutic) to be delivered to a tissue of interest. The modified purified caveolae are introduced into an individual in need of the agent by an appropriate route such as intravenously, intramuscularly, topically, or by inhalation spray. For example, modified caveolae containing an agent can be administered into the lungs of an individual in need of a chemotherapeutic agent for lung cancer by an aerosol or inhalation spray. In the lung tissue, the caveolae act as delivery vehicles and the agent is delivered to the affected cells.

The invention is further illustrated by the following Examples, which are not limiting in any way.

EXAMPLES

When cells are isolated from tissues and grown in culture, there can be a substantial loss of caveolae from the cell surface, especially for endothelial cells (J. E. Schnitzer et al., *Biochem. Biophys. Res. Commun.* 199:11 (1994). Such losses (often >100-fold) represent a substantial alteration in plasma membrane organization and may reflect a major perturbation in caveolar function and even GPI-linked protein clustering. Thus, the relationship between GPI-anchored proteins and caveolae was explored under conditions to avoid potential influences of cell culture, and also to avoid antibody effectors and contamination from intracellular compartments.

All of the membrane subfractions described herein were isolated after exposure to detergent in order to be consistent and limit the number of variables in the comparison of the subfractions. However, caveolae can be sheared and isolated from silica-coated membrane pellets without detergent, although less efficiently. As noted in (Kurzhalia, T. V., et al., *Trends Cell Biol.* 5:187–189 (1995)), the usual protocol was followed for caveolae isolation, with the exception that Triton X-100 was omitted and, for shearing purposes, the number of homogenization strokes was increased to 48 or 60 from 12.

The following methods and materials were used to selectively isolate the luminal endothelial plasmalemma with its subtending caveolae from rat lung microvasculature and to purify caveolae from the plasmalemmal fraction.

Methods

Antibodies

Mouse monoclonal antibody to caveolin was from Zymed or Transduction Laboratories (Lexington, KY); rabbit polyclonal antibody to angiotensin converting enzyme (ACE) was from R. Skidgel (University of Illinois); rabbit polyclonal antibody to band 4.1, from V. Marchesi (Yale University); mouse monoclonal antibody to $Ca^{2+}$-ATPase, from Affinity BioReagents (Neshanic Station, N.J.); mouse monoclonal antibody to β-actin, from Sigma; and goat polyclonal antibody to $IP_3$ receptor, from Solomon H. Snyder and Alan Sharp (Johns Hopkins University). Sources for other reagents were as before (Schnitzer, J. E., et al., *J. Cell Biol.* 127:1217 (1994); Schnitzer, J. E. and Bravo, J., *J. Biol. Chem.* 268:7562 (1993); Schnitzer, J. E. and Oh, P., *J. Biol. Chem.* 269:6072 (1994); and Jacobson, B. S., et al., *Eur. J. Cell Biol.* 58:296 (1992)).

In Situ Perfusion of Rat Lungs for Silica Coating of the Luminal Endothelial Cell Surface The lungs of anesthetized male Sprague-Dawley rats were ventilated after tracheotomy and then perfused as described (Schnitzer, J. E. and Oh, P., *J. Biol. Chem.* 269:2072 (1994); Jacobson, B. S., et al., *Biochem. Biophys. Res. Commun.* 199:11 (1994)). In brief, the right cardiac ventricle was injected with 0.5 ml of Ringer's solution at pH 7.4 (111 mM NaCl/2.4 mM KCl/1 mM $MgSO_4$/5.5 mM glucose/5 mM Herpes/0.195 mM $NaHCO_3$) containing 30 μM nitroprusside and 175 units of heparin before cannulation of the pulmonary artery. The lungs were perfused at 8–10 mmHg (1 mmHg=133 Pa) with the following solutions (all at 10–12° C. except as noted) in order: (i) oxygenated Ringer's solution containing 30 μM nitroprusside for 90 sec at room temperature and then for 3.5 min at 10–12° C.; (ii) MBS (125 mM NaCl/20 mM Mes, pH 6.0) for 90 sec; (iii) 1% colloidal silica in MBS; (iv) MBS for 90 sec, to clear free silica from vasculature; (v) 1% sodium polyacrylate in MBS for 90 sec, to crosslink and shield membrane-bound silica; and (vi) 8–10 ml of Hepes-buffered sucrose with protease inhibitors [HBS+, pH 7, contains 0.25M sucrose, 25 mM Hepes, leupeptin (10 μg/ml), pepstatin A (10 μg/ml), o-phenanthroline (10 μg/ml), 4-(2-aminoethyl) benzenesulfonyl fluoride (10 μg/ml), and trans-epoxysuccinyl-L-leucinamido(4-guanidono)butane (50 μg/ml)]. The lungs were excised and immersed in cold HBS+.

Purification of Luminal Endothelial Cell Membranes

The chilled rat lungs were weighed, minced with a razor blade in a plastic dish on an aluminum block embedded in crushed ice, and then added to 20 ml of cold HBS+ for homogenization (12 strokes) in a type C Teflon pestle/glass homogenizer with a high-speed rotor run at 1800 rpm. After filtration through a 0.53-μm NYTEX net followed by a 0.3-μm net, the homogenate was mixed with 102% (wt/vol) NYCODENZ (Accurate Chemical and Scientific) with 20 mM KCl to make a 50% final solution and was layered over a 55–70% NYCODENZ continuous gradient containing 20 mM KCl plus HBS. After centrifugation in a Beckman SW28 rotor at 15,000 rpm for 30 min at 4° C., the pellet was suspended in 1 ml of MBS and named P.

Purification of Caveolae from Silica-Coated Endothelial Cell Membranes

Cold 10% (vol/vol) Triton X-100 was added to the suspended membrane pellet (P) as described above to make a final concentration of 1%. After nutation for 10 min at 4° C., the suspension was homogenized in a type AA Teflon pestle/glass homogenizer (10 strokes) and then brought to 40% sucrose and 20 mM KCl. A 35–0% sucrose gradient in 20 mM KCl was layered over the homogenate in a Beckman SW55 rotor tube and then centrifuged at 4° C. overnight at 30,000 rpm. A membrane layer clearly visible between 10% and 16% sucrose was collected, labeled V, and then diluted 3-fold with MBS before centrifugation for 2 hr at 13,000×g at 4° C. The resultant pellet was either processed for electron microscopy or for further analysis. In attempting to optimize the conditions for isolation of caveolae, it was found that the low-density caveolar fraction was not altered by (i) the presence of TRITON X-100 throughout the sucrose gradient during centrifugation and (ii) the absence of TRITON X-100 during homogenization, except that the yield of caveolae was diminished. TRITON X-100 appears to facilitate the shearing of the caveolae away from the plasma membrane.

ELISA

After the sucrose density centrifugation described above, 33 fractions of 150 μl were collected and the pellet was suspended in 150 μl of MBS (fraction 34). Aliquots of each fraction (50–100 μl) were placed in individual wells of a 96-well tray for drying overnight. After washing, the wells were blocked for 1 hr with ELISA wash buffer (EWB: 2% ovalbumin/2 mM $CaCl_2$/164M NaCl/57 mM phosphate, pH 7.4), incubated for 1 hr with EWB containing antibodies (1:200) to either caveolin or ACE, washed for 1 min in EWB three times, incubated with reporter antibody conjugated to horseradish peroxidase (1:500 in EWB), and washed again. Substrate solution (50 mM $Na_2HPO_4$/25 mM citric acid/ 0.12% o-phenylenediamine dihydrochloride/0.03% $H_2O_2$) was added and the reaction was stopped with 4 M $H_2SO_4$ before the signal was read with a Molecular Devices THERMOMAX microplate reader.

SDS/PAGE and Immunoblotting

As reported ((Sargiacomo, M., et al., *J. Cell. Biol.* 122:789 (1993); Lisanti, M. P., et al., *J. Cell. Biol.* 123:595 (1993); Montessano, R., et al., *Nature* 296:651 (1982)), the proteins of various tissue fractions were solubilized and separated by SDS/PAGE in 5–15% gels for direct analysis by silver staining or electrotransfer to nitrocellulose or poly(vinylidene difluoride) (IMMOBILON; Millipore) filters for immunoblotting using primary antibodies followed by appropriate $^{125}$I-labeled reporter antibodies. Band intensities were quantified by PHOSPHORIMAGER (Molecular Dynamics), densitometry of autoradiograms, and/or direct counting of γ radioactivity. Protein assays were performed with the Bio-Rad BCA kit.

EXAMPLE 1

Isolation of Coated Membrane Pellets (P)

Isolation of caveolae associated with the endothelial cell surface has many difficulties. The endothelium represents but a small percentage of a diverse population of cells in any organ. Unfortunately, isolating endothelial cells from tissues as a primary source or even for growth in culture causes morphological changes, including a very significant loss in cell surface caveolae (Schnitzer, J. E., et al., *Biochem. Biophys. Res. Commun.* 199:11 (1994)). Also, noncoated vesicles that are very similar in size and density to plasmalemmal caveolae and may even contain the caveolar marker protein caveolin (Dupree, P., et al., *EMBO J.* 12:1597 (1993); Kurzchalia, T. V., et al., *J. Cell Biol.* 118:1003 (1992)), may be found in other cellular compartments such as the trans-Golgi network. Moreover, caveolae may vary according to cell type (Izumi, T., et al., *J. Electron Microsc.* 38:47 (1989)). To overcome the above problems, a strategy of first isolating in high yield and purity the luminal endothelial plasma membranes with associated caveolae from rat lungs in situ was used. The caveolae were then removed and isolated from this membrane fraction.

Purification of Luminal Endothelial Cell Membranes from Rat Lungs Perfused in Situ The rat lung microvasculature was perfused via the pulmonary artery with a positively charged colloidal silica solution to coat the luminal endothelial cell membrane normally exposed to the circulating blood and create a stable adherent silica pellicle that marks this specific membrane of interest (Jacobson, B. S., et al., *Eur. J. Cell. Biol.* 58:296 (1992)). Such a coating increased the membrane's density and was so strongly attached to the plasma membrane that after tissue homogenization, large sheets of silica-coated membrane with attached caveolae were readily isolated away from other cellular membranes and debris by centrifugation through a high-density medium (Jacobson, B. S., et al., *Eur. J. Cell. Biol.* 58:296 (1992)). The silica-coated membranes displayed ample enrichment for endothelial cell surface markers and little contamination from other tissue components. As shown in past work (Jacobson, B. S., et al., *Eur. J. Cell. Biol.* 58:296 (1992)), the typical isolated membrane sheet had caveolae attached on one side and a silica coating on the other side. By SDS/PAGE, the silica-coated membranes had a protein profile quite distinct from that of the starting lung homogenate. Moreover, quantitative immunoblotting revealed enrichments up to 30-fold in the silica-coated membrane pellets relative to the starting tissue homogenate for several proteins known to be expressed on the surface of endothelium, such as caveolin (Dupree, P., et al., *EMBO J.* 12:1597 (1993)) and ACE (Caldwell, P. R. B., et al., *Science* 191:1050 (1976)). Conversely, proteins of intracellular organelles (cytochrome oxidase and ribophorin) and even the plasma membranes of other lung tissue cells (fibroblast surface antigen) were excluded from this membrane fraction.

Detergent Resistance of Caveolin as a Marker for Caveolae

Caveolin was used as a biochemical marker for caveolae; it was found that the caveolin abundantly expressed in the silica-coated membranes was resistant to solubilization by homogenization at 4° C.–8° C. using TRITON X-100 or 3-[(3-cholamidopropyl)dimethylammonio]-1-propanesulfonate but not other detergents, including octyl β-D-glucoside, SDS, deoxycholate, and Nonidet P-40. SDS/PAGE revealed that many proteins in silica-coated membranes were solubilized by TRITON X-100, whereas others were not and could be sedimented by centrifugation. Immunoblotting showed that caveolin and the cytoskeletal protein band 4.1 were sedimented into the Triton-insoluble fraction, whereas ACE was found primarily in the TRITON-soluble fraction.

EXAMPLE 2

Isolation of Purified Caveolae (V)

Caveolae attached on the cytoplasmic side of the plasma membranes, opposite to the silica coating in the silica-coated membrane pellets (P), were stripped from the membranes by shearing during homogenization at 4° C. in the presence or absence of TRITON X-100. They were then isolated by sucrose density gradient centrifugation to yield a homogenous population of biochemically and morphologically distinct caveolar vesicles (V). This technique is represented schematically in FIG. 1.

Isolation of Vesicles Stripped From Silica-Coated Membranes

The silica-coated membranes (P) in TRITON X-100 were stripped of protruding caveolae by shearing in a homogenizer and then subjected to sucrose density centrifugation to isolate the caveolae. Analysis of 34 fractions from the sucrose gradient revealed a peak signal for caveolin well separated from that for ACE. Little caveolin was detected in the silica-coated membrane after removal of the vesicles (P-V). Most of it was in the visible membrane band at 10–16% sucrose (fractions 6–10), which was collected, labeled V for vesicles, and examined by electron microscopy, SDS/PAGE, and immunoblotting.

Characterization of Isolated Vesicles as Caveolae Electron microscopy was performed (as in Dvorak, A. M., *J. Electron Microsc. Tech.* 6:255 (1987)) on the three main membrane fractions: original silica-coated membrane (P), isolated vesicles (V), and the silica-coated membrane pellet after removal of vesicles (P-V). In P, small, membrane-bound electron-lucent openings, or fenestrae, were visible in many vesicles in favorable sections and clearly were not part of the ostia of the caveolae directly at the cell membrane surface. These fenestrae, as described many years ago (Palade, G. E. and Bruns, R. R., *J. Cell Biol.* 37:633 (1968)), are characteristic of endothelial caveolae and probably indicate a previous attachment to another vesicle as part of a chain of vesicles. The P-V fraction contained silica-coated membranes without attached caveolae. The V fraction contained a rather uniform distribution of small noncoated vesicles, primarily with diameters of 50–100 nm. Higher magnification revealed vesicular structures typical for caveolae in vivo. Single plasmalemmal vesicles and chains of membrane-bound vesicles were present. The fenestrae distinctive for caveolae were easily visible in many of the vesicles. Some vesicles still maintained their narrowed necks as in caveolae that are attached to the plasmalemma of endothelium in vivo. Higher magnification showed central, membrane-bound fenestrae within the isolated caveolae. Central dense, rounded knobs as described originally in vivo (Palade, G. E. and Bruns, R. R., *J. Cell Biol.* 37:633 (1968)) could be found within some of these fenestrae (unpublished observations).

Figure 4:
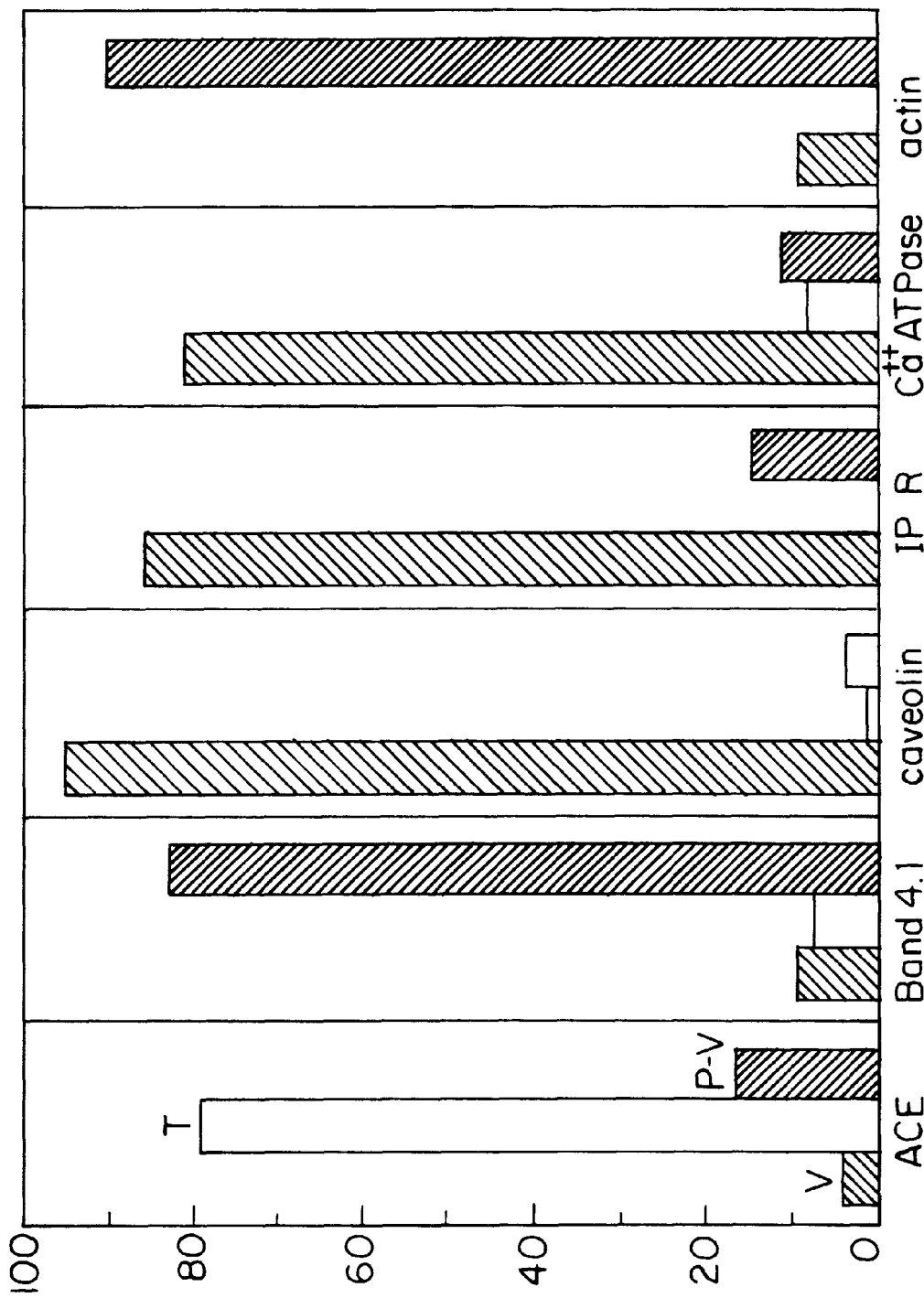
FIG. 4 is a graphic representation of the percent distribution of specific proteins in plasma membrane subfractions.

Biochemical analysis revealed a distinct protein profile for the isolated vesicles, with not only very evident enrichment of various proteins relative to the starting membrane pellet but also exclusion of other proteins. Immunoblotting showed a significant enrichment in V for caveolin, plasmalemmal $Ca^{2+}$-ATPase, and $IP_3$ receptor, with up to a 13-fold enrichment for caveolin and $IP_3$ receptor relative to original membrane (Table). Furthermore, little signal for these proteins remained behind in the silica-coated membrane (P-V) after the caveolae were removed. Immunoblots that were quantified revealed that these three integral membrane proteins were resistant to TRITON solubilization and concentrated within the purified caveolae (FIG. 4). Eighty to 95% of the signal for the $Ca^{2+}$ pump, $IP_3$ receptor, and caveolin was within the caveolar fraction. By contrast, band 4.1 and ACE were excluded. These purified caveolae represented a microdomain of the plasma membrane with at least three resident proteins that were not just freely distributed over the whole cell surface but preferentially localized to this organelle.

The extent of purification of caveolae is indicated by the relative enrichments for caveolin (Table). As far as yields, it was previously shown that >90% of the microvasculature in situ was coated with silica and at least 80% of the silica-coated membrane was pelleted from the rat lung homogenates (Jacobson, B. S., et al., *Eur. J. Cell. Biol.* 58:296 (1992)). The recovery of caveolin in the membrane pellet (P) was 10% of the total detected in the starting homogenate, which was consistent with the concept that only the plasmalemmal subset of caveolin-containing vesicles from the luminal side of the endothelium was isolated. The yield of plasmalemmal caveolae derived directly from the original silica-coated membranes (P) ranged from 53% to 60% over four separate experiments as indicated by ELISA and immunoblotting for caveolin. Overall, about 5 μg of total protein were isolated, which represented about 5–6% of the caveolae in the starting lung homogenates.

TABLE

Relative Distribution of Various Proteins in Rat Lung Fractions

| Antigen | Pellet/homogenate | Vesicle/pellet |
| --- | --- | --- |
| ACE | 15 | 0.08 |
| Caveolin | 30 | 13 |
| Fibroblast surface antigen | 0 | — |
| $Ca^{2+}$-ATPase | 8 | 3 |
| $IP_3$ receptor | 3 | 12 |
| Band 4.1 | 15 | 0.09 |
| Cytochrome oxidase | 0 | — |
| Ribophorin | 0 | — |

Data represent a composite of new experiments/antigens and previously reported results (Jacobson, B. S., et al., Eur. J. Cell. Biol. 58:296 (1992)). Quantified band intensities of immunoblots were normalized per unit of protein before computation of ratios as an average of at least two determinations.
The value 0 indicated antigen not detected in P but found in H;
— indicates not done.

EXAMPLE 3
Isolation of Microdomains of GPI-Anchored Proteins (G)

The silica coating of the outer membrane surface altered the way in which the GPI-anchored proteins interacted with various detergents and thus prevented the separation of noncaveolar, detergent-resistant microdomains from the cell membranes. Cationic silica particles interact with the anionic cell surface to stabilize it against vesiculation or lateral rearrangement by immobilizing membrane molecules (Chaney, C.K. and Jacobson, B. S., J. Biol. Chem. 258:10062 (1983); Patton, W. F., et al., Electrophoresis 11:79 (1990)). Because the silica particles uniformly coated the cell surface but were rarely associated with or present inside the caveolae because of their size, it is likely (Schnitzer, J. E., et al., Proc. Natl. Acad. Sci. USA 92:1759 (1995); Jacobson, B. S., et al., Eur. J. Cell Biol. 58:296 (1992)) that the plasma membrane was stabilized by being firmly attached on one side to most, if not all, nonvesiculated regions. This adherent pellicle allowed the caveolae on the opposite side of the membrane to be sheared away by homogenization, with little contamination from other membranes, including other detergent-resistant domains. Conversely, without silica coating, both caveolar and non-caveolar detergent-resistant membranes were co-isolated.

Because the silica coating prevented the release of the detergent-insoluble membranes rich in GPI-anchored proteins, it was possible to isolate these domains separately from the caveolae. A method by which this was carried out is represented schematically in FIG. 2. Silica-coated membranes stripped of caveolae (P-V) were incubated with 2M $KH_2PO_4$, followed by homogenization in TRITON X-100 at 4° C. This procedure allowed the isolation by sucrose density gradient centrifugation of a membrane fraction (G) that contained vesicles of >150 nm in diameter with no caveolae by morphological and biochemical criteria (data not shown).

EXAMPLE 4
Isolation of a Membrane Fraction Comprising Caveolae and Microdomains of GPI-Anchored Proteins (TI)

Figure 3:
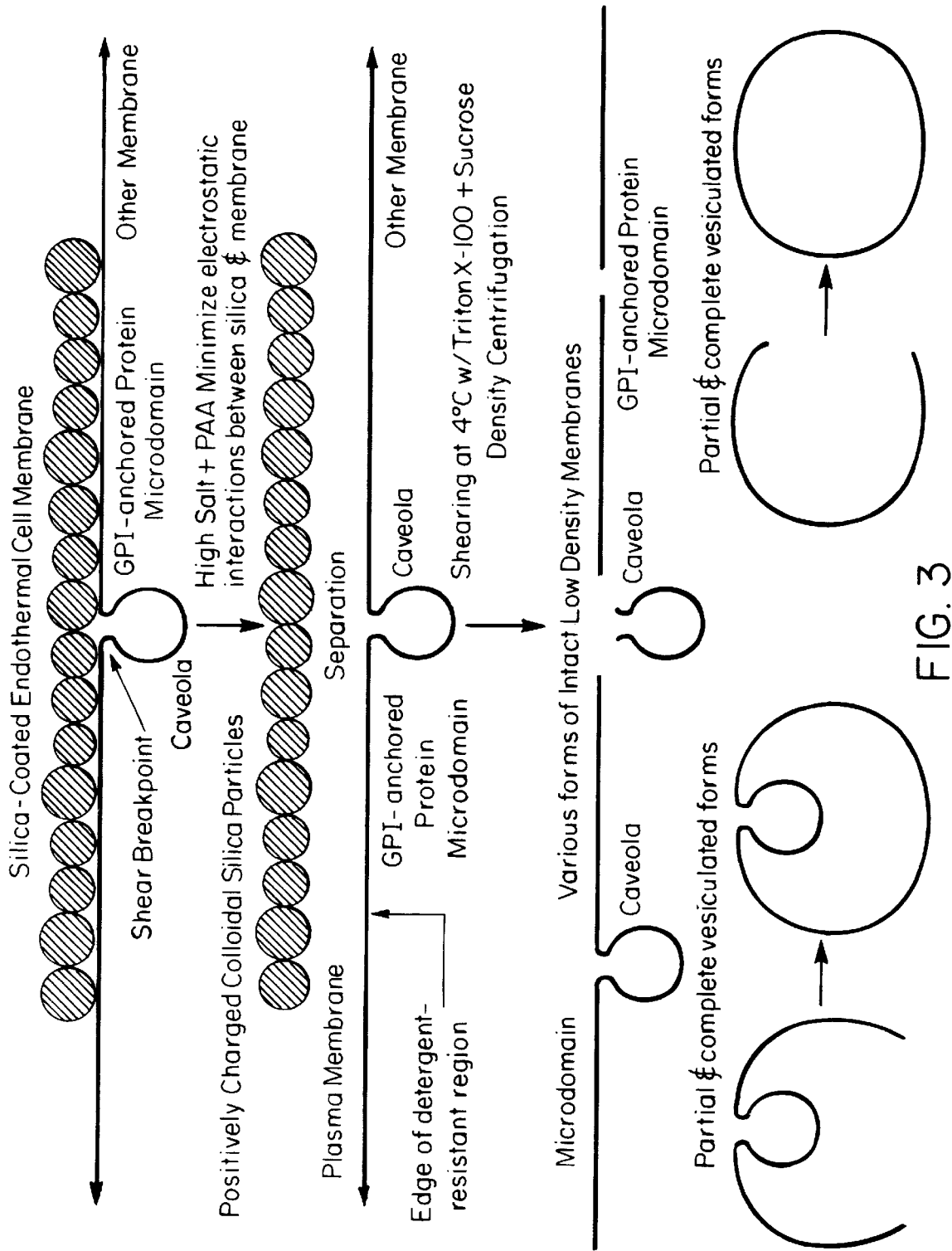
FIG. 3 is a schematic representation of isolation of caveolae associated with GPI-anchored protein microdomains.

Methods similar to those described above were used to isolate a membrane fraction which contained caveolae, G domains, and caveolae associated with G domains, as represented schematically in FIG. 3. The salt concentration was increased during the isolation of the silica-coated membrane pellicles, which sufficiently reduced electrostatic interactions between the cationic silica particles and the polyanionic cell surface to detach the plasma membrane from the silica-coated membrane pellicle in (P). Under these conditions, intact membranes were separated, and, with the addition of TRITON X-100, low density, detergent-resistant membranes (TI) were isolated by sucrose density gradient centrifugation, as described above.

EXAMPLE 5
Protein Analysis of Various Membrane Subfractions

Differential detergent extraction was performed on silica-coated endothelial cell membranes (P). Equal portions of resuspended P were incubated with rotation for 1 hour at 40° C. with various detergents (β-OG, β-octylglucoside; sodium deoxycholate; TRITON X-100) before centrifugation at 13,000 g for 2 hours. The soluble proteins (S) and the sedimented,insoluble proteins (I) were fractionated by SDS-polyacrylamide gel electrophoresis (10 μg/lane), transferred to nitrocellulose or IMMOBILON (Millipore) filters, and subjected to immunoblot analysis with equivalent amounts of specific antibodies for caveolin, 5'-NT, Band 4.1, GM, and uPAR and the appropriate 125-I-labeled secondary antibodies as described (Schnitzer, J. E. and Oh, P., J. Biol. Chem. 269:6072 (1994); Milci, A. J., et al., J. Cell Biol. 105:2603 (1987)). Other proteins tested included angiotensin-converting enzyme, which was solubilized by all of these detergents, and carbonic anhydrase, which was solubilized similarly to 5'-NT (unpublished data). Proteins from rat lung homogenate (H), the TRITON X-100-insoluble membranes isolated by sucrose density gradient centrifugation (TI), and the sedimented pellet (R) were also subjected to immunoblot analysis as above, with the exception that the secondary antibodies were conjugated to horseradish peroxidase (HRP) and binding was detected with ECL chemiluminescent substrate (Amersham).

Figure 5A:
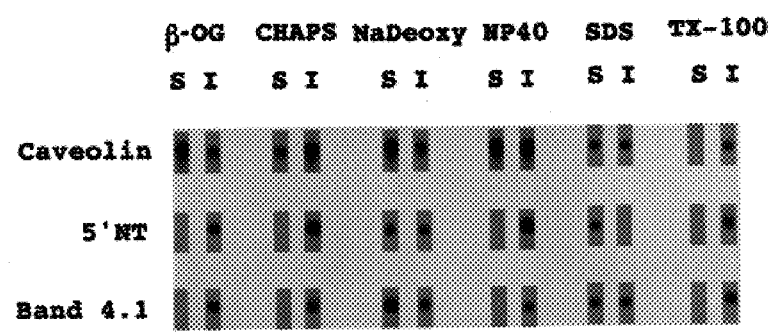
FIGS. 5A–5E are a series of photographs showing results of protein analysis of various membrane subfractions.
Figure 5B:
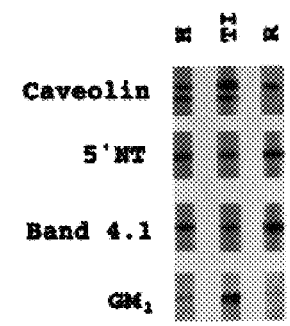

Detergent extraction studies performed on P revealed differences in the ability of various detergents to solubilize caveolin and 5'-nucleotidase (5'-NT). Caveolin was partially solubilized by β-octyl glucoside, CHAPS, deoxycholate, NP-40, and SDS (but not TRITON X-100), whereas 5'-NT was rendered soluble only by SDS and deoxycholate (FIG. 5A). Isolations with rat lung tissue, performed as in Lisanti, M. P., et al. (J. Cell. Biol. 126:111 (1994)), demonstrated that caveolin and GPI-anchored proteins (in this instance, 5'-NT) were both present in the isolated TRITON X-100-insoluble membranes (TI) (FIG. 5B), consistent with previous studies (Sargiacomo, M., et al., J. Cell. Biol. 122:769 (1993); Lisanti, M. P., et al., J. Cell. Biol. 123:595 (1993); Change, W.-J., et al., J. Cell Biol. 126:127 (1994); and Lisanti, M. P., et al., J. Cell Biol. 126:111 (1994)). The differential detergent extraction studies performed on TI demonstrated that GPI-anchored proteins were solubilized effectively by β-octyl glucoside, CHAPS, deoxycholate, and SDS, as expected (Brown, D. A. and Rose, J. K., Cell 68:533 (1992); Letarte-Murhead, M., et al., Biochem. J. 143:51 (1974); Hoessli, D. and Runger-Brandle, E., Exp. Cell. Res. 166:239 (1985); Hooper, N. M. and Turner, A. J., Biochem. J. 250:865 (1988); Sargiacomo, M., et al., J. Cell. Biol. 122:789 (1993); Lisanti, M. P., et al., J. Cell. Biol. 123:595 (1993)). This pattern was different from the pattern of solubility for 5'-NT in P but similar to that for caveolin in P.

Figures 5C, 5D, 5E:
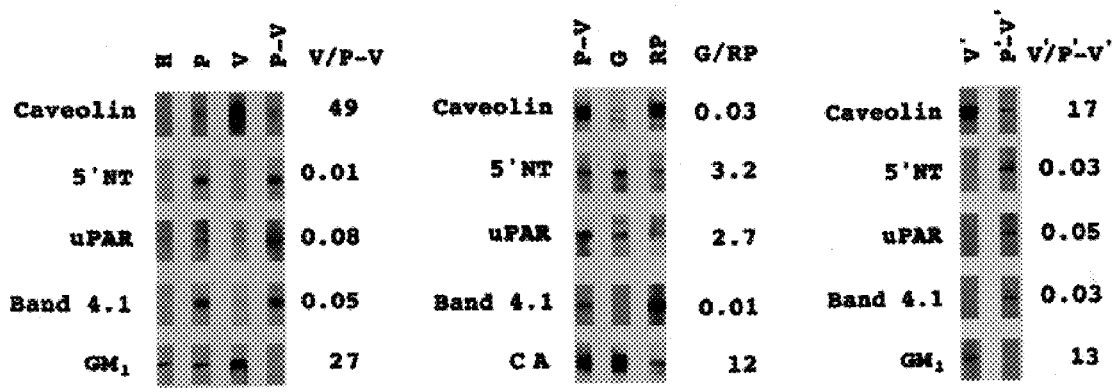

The lack of GPI-anchored proteins in the purified caveolae enriched in caveolin and ganglioside $GM_1$ was also demonstrated. The lipid-anchored, cholera toxin-binding ganglioside $GM_1$ has been localized with gold labeling inside the caveolae (Parton, R. G., J. Histochem. Cytochem. 42:155 (1994); Montessano, R., et al., Nature 296:651 (1982)), and was thus used as a caveolar marker. Whole-lung homogenate (H), silica-coated luminal endothelial membranes (P), purified caveolae (V), and the resedimented silica-coated membranes after stripping of the caveolae (P-V) were subjected to immunoblot analysis as above. $GM_1$ was detected not only by immunoblotting but also by direct blotting with HRP-conjugated cholera toxin. Ratios of the signals detected in V versus P-V are shown in FIG. 5C. V contained >90% of $GM_1$ (FIG. 5C). The remaining membrane devoid of caveolae lacked detectable $GM_1$, although it was rich in GPI-anchored proteins. Furthermore, like caveolin, 5'-NT and urokinase-plasminogen activator receptor (uPAR) were enriched in P relative to the starting rat lung homogenate (H) (FIG. 5C). However, unlike caveolin, these proteins were not enriched in V; they remained almost totally associated with the resedimented silica-coated membranes stripped of the caveolin (P-V) which contain few, if any, remaining caveolae. More than 95% of the signal for caveolin was detected in V, with <4% remaining in P-V. Conversely, >95% of 5'-NT and uPAR remained in P-V, with <3% present in V. Thus, these GPI-anchored proteins were neither coupled to caveolin nor concentrated in the isolated, caveolin-enriched caveolae. Thus, as with caveolae present on the endothelial cell surface in vivo (Kurzchalia, T. V., et al., *J. Cell Biol.* 118:1003 (1992); Dupree, P. l, et al., *EMBO J.* 12:1597 (1993); Rothberg, K. G., et al., *Cell* 68:673 (1992); Fujimoto, T., et al., *J. Cell. Biol.* 119:1507 (1992); Fujimoto, T., *J. Cell. Biol.* 120:1147 (1993)), the purified caveolae (V) were enriched in caveolin, plasmalemmal $Ca^{2+}$-dependent adenosine triphosphatase, and the inositol 1,4,5-triphosphate receptor. In contrast, other markers present amply in P, including angiotensin-converting enzyme, band 4.1, and β-actin, were almost totally excluded from V.

The GPI-anchored protein which was isolated separately from the silica-coated membranes was also subjected to immunoblot analysis. Results are shown in FIG. 5D. Immunoblot analysis was performed as described above, with P-V, from the silica and RP (the resedimented pellet of silica-containing material). The silica-coated membrane pellet already stripped of caveolae (P-V) was resuspended in 20 mM 2-IN-morpholino) ethenesulfonic and with 125 mM NaCl and an equal volume of 4M $K_2HPO_4$ and 0.2% polyacylate (pH 9.5). The solution was sonicated (10 10-s bursts) with cooling, mixed on a rotator for 8 hours at room temperature (20° C.), and sonicated again (five 10-s bursts). Triton X100 was added to 1%, and the preparation was then mixed for 10 min at 4° C. and homogenized with a Type AA Teflon tissue grinder (Thomas Scientific, Swedesboro, N.J.). Any intact floating detergent-resistant membranes were separated and isolated from this homogenate by sucrose density gradient centrifugation as above. The caveolin in P-V is equivalent to that seen in FIG. 5C, representing the small residual signal after stripping of the caveolae (compare V and P-V), except that the exposure here is much longer. $GM_1$ could not be detected in P-V (see FIG. 5C)), nor, as expected, in G or RP (data not shown). G is rich in GPI-linked proteins (5'-NT, uPAR and CA) but lacks caveolin and $GM_1$. Control experiments performed identically but without high salt did not yield any detectable membranes in the sucrose gradient (data not shown). G lacked caveolin but was enriched in several GPI-anchored proteins: 5'-NT, uPAR, and carbonic anhydrase (CA) (FIG. 5D). These results demonstrated that distinct detergent-resistant plasma membranes rich in GPI-anchored proteins but lacking caveolin were isolated separately from the caveolae. Similar detergent-resistant membranes, consisting of large vesicles rich in GPI-anchored proteins but devoid of caveolin, have also been isolated from lymphocytes and neuroblastoma cells, both of which lack caveolae and do not express caveolin (Fra, A. M., et al., *J. Biol. Chem.* 269:30745 (1994); Gorodinsky, A. and Harris, D. A., *J. Cell Biol.* 129:619 (1995)).

Immunoblot analysis of caveolae isolated without TRITON X-100 was also conducted. Caveolae were purified without any exposure to detergent. As noted above, caveolae can be isolated without exposure to TRITON X-100, but less efficiently. The usual protocol was followed for caveolae isolation, with the exception that TRITON X-100 was omitted and, for shearing purposes, the number of homogenization strokes was increased to 48 to 60 from 12). These caveolae (V') and the membrane stripped of them (P'-V') were subjected to immunoblot analysis as in FIG. 5B. The results, shown in FIG. 5E, were consistent with those obtained from caveolae purified without detergent: caveolin and $GM_1$ were enriched in V' whereas GPI-anchored proteins were almost completely excluded from detergentfree purified caveolae (V').

Other studies that have examined membrane diffusion by fluorescence recovery after photobleaching have detected a larger fraction of GPI-anchored proteins (20 to 60%) present in an immobile fraction (Hannan, L. A., et al., *J. Cell. Biol.* 120:353 (1993); Brown, D. A. and Rose, J. K., *ell* 68:533–544 (1992); Zhang, F., et al., *J. Cell. Biol.* 115:75 (1991); Zhang, F., et al., *Proc. Natl. Acad. Sci. USA*, 89:5231 (1992)). By examination of detergent solubility, similar percentages have been detected for the GPI-linked proteins in the detergent-resistant microdomains, suggesting equivalence of this fraction with the immobile fraction detected in the diffusion studies. Specialized glycolipid domains are resistant to detergent extraction and are necessary for maintaining detergent-resistant clusters of GPI-linked proteins (Schroeder, R., et al., *Proc. Natl. Acad. Sci. USA*. 91:12130 (1994); Brown, D. A. and Rose, J. K., *Cell* 68:533 (1992); Letarte-Murhead, M., et al., *Biochem. J.* 143:51 (1974); Hoessli, D. and Runger-Brandle, E., *Exp. Cell. Res.* 166:239 (1985); Hooper, N. M. and Turner, A. J., *Biochem. J.* 250:865 (1988); Sargiacomo, M., et al., *J. Cell. Biol.* 122:789 (1993); Lisanti, M. P., et al., *J. Cell. Biol.* 123:595 (1993)). Removal of cholesterol from plasma membranes can dissociate or prevent the formation of such clusters and assure a random, free distribution of GPI-anchored proteins (Rothberg, K. G., et al., *J. Cell Biol.* 111:2931 (1990)). As expected, cholesterol removal reduces the resistance of GPI-linked proteins to detergent solubilization (Sargiacomo, M., et al., *J. Cell. Biol.* 122:789 (1993); Lisanti, M. P., et al., *J. Cell. Biol.* 123:595 (1993)), consistent with the notion that the freely diffusing GPI-anchored proteins are indeed more readily solubilized by detergent than the less mobile GPI-anchored proteins in the glycolipid domains. Moreover, in the absence of glycolipids, GPI-anchored proteins are readily solubilized from membranes by cold TRITON X-100; solubility decreases with the addition of appropriate glycolipids (Schroeder, R., et al., *Proc. Natl. Acad. Sci. USA*. 91:12130 (1994)). Thus, GPI-anchored proteins randomly distributed at the cell surface should be susceptible to detergent extraction; indeed, the percentages shown herein agree with those from the diffusion studies. In homogenates of non-silica-coated rat lung, approximately 60% of CA and 75% of 5'-NT are solubilized by TRITON X-100 at 4° C. Moreover, mass balances performed on the silica-coated membranes showed that approximately 20% of 5'-NT and 40% of CA could be isolated in the intact, detergent-resistant membrane fraction TI.

Thus, it appears that a substantial but variable fraction of GPI-anchored proteins exists on the cell surface dynamically partitioned into detergent-resistant glycolipid microdomains that are not likely to be simply a consequence of detergent extraction, and that the size of this fraction may depend on cell type, culture, and ligand or antibody exposure.

Lipid anchors such as GPI may control the ability of proteins to partition selectively, but reversibly, within the specialized microdomains and, therefore, may subserve a targeting function. The GPI anchor directly affects association with detergent-resistant membranes (Rodgers, W., et al., *Mol. Cell. Biol.* 14:5364 (1994)), membrane diffusion (Hannan, L. A., et al., *J. Cell. Biol.* 120:353 (1993); Zhang, F., et al., *J. Cell. Biol.* 115:75 (1991); Zhang, F., et al., *Proc. Natl. Acad. Sci. USA*, 89:5231 (1992)), polarized delivery to cell surfaces (Brown, D., et al., *Science* 245:1499 (1989); Simons, K. and van Meer, G., *Biochemistry* 27:6197 (1988); Garcia, M., et al., *J. Cell Sci.* 104:1281 (1993)), cell activation (Su, B., et a., *J. Cell Biol.* 112:377 (1991)), and the rate and pathway of internalization (Keller, E.-A., et al., *EMBO J.*, 3:863 (1992)). Other lipid-associated proteins, including NRTKs and guanosine triphosphate (GTP)-binding proteins such as RabS, are found in the detergent-resistant complexes (Sargiacomo, M., et al., *J. Cell. Biol.* 122:789 (1993); Lisanti, M. P., et al., *J. Cell. Biol.* 123:595 (1993); Chang, W.-J., et al., *J. Cell. Biol.* 126:127 (1994); Lisanti, M. P., et al., *J. Cell. Biol.* 126:111 (1994); Rodgers, W., et al., *Mol. Cell. Biol.* 14:5364 (1994); Arreaza, G., et al., *J. Biol. Chem.* 269:19123 (1994); Shenoy-Scaria, A. M., et al., *J. Cell Biol.* 126:353 (1994)). The current analysis reveals that various NRTKs (Yes and Lyn, unpublished data) heterotrimeric GTP-binding proteins ($\alpha$ and $\beta\gamma$ subunits) (Schnitzer, J. E., et al., *J. Biol. Chem.* 270:14399 (1995)), and as yet unidentified small GTP-binding proteins, but not RabS (Schnitzer, J. E., et al., *J. Biol. Chem.* 270:14399 (1995)), are indeed present in purified caveolae.

EXAMPLE 6
Electron Microscopy of V and TI Preparations

Preparations V and TI were examined under electron microscopy to determine whether caveolae were equivalent with low density, TRITON insoluble membranes. The electron microscopy was performed on membrane isolates as described in Schnitzer, J. E. et al., *Proc. Natl. Acad. Sci., USA*, 92:1759–1763 (1995), the teachings of which are incorporated herein by reference.

Electron microscopy of the vesicles (V) purified from the silica-coated rat lung endothelial membranes showed that the V isolate shows a homogenous population of small vesicles ($\leq 100$ nm) with typical caveolar morphology. Despite the isolation procedure, many caveolae retained their characteristic flask shape.

The detergent-resistant membranes (TI) isolated without silica coating consisted of many larger vesicles (>150 and <700 nm in diameter) interspersed with smaller caveolar vesicles (<100 nm) and some nonvesiculated, linear membrane sheets. A typical caveola was often apparent attached to the inside of a larger vesicle. In many favorable cross-sections, a characteristic flask-shaped caveola attached to a larger, spherical vesicle was apparent, suggesting that these two detergent-resistant membrane domains were associated with each other as a unit before fractionation in the membrane.

EXAMPLE 7
Colloidal Gold Immunolabeling

Detergent-resistant membrane isolates (TI) were embedded in agarose for gold labeling of CA or $GM_1$. The lipid-anchored molecule, the cholera toxin-binding ganglioside $GM_1$, has been localized with gold labeling inside the caveolae (Parton, R. G., *J. Histochem. Cytochem.* 42:155 (1994); Montesano, R., et al., *Nature* 296:651 (1982)), and was therefore used as a marker for caveolae. Overall, a size criterion was obvious in distinguishing the caveolar vesicles from the noncaveolar vesicles. Therefore, the vesicles clearly observed in the electron micrographs were divided into two groups: those with diameters of <80 nm and those with diameters of >150 nm. This size criterion cannot be considered absolute in separating caveolae from noncaveolar vesicles, because, for instance, a few caveolae could remain attached to each other and form a larger vesicle. Nevertheless, the results of immunolabeling supported the use of $GM_1$ as a caveolar marker, and substantiated the size criterion.

At low magnification, immunogold labeling of TI localized CA primarily on the surface of the larger vesicles and linear membranes but not on the smaller caveolae. All gold is attached to membranes with little, if any, background labeling. At higher magnification, images revealed unlabeled caveolae apparently attached to large vesicles labeled with gold or associated with labeled membrane strands attached to the neck of the caveolae. Control experiments with nonimmune serum showed little labeling of membranes; only an occasional gold particle was detected per field examined and appeared equivalent to background labeling of agarose alone. In contrast, higher magnification micrographs revealed that immunogold labeling for $GM_1$ was frequently detected inside the caveolae, with little labeling of the caveolae-associated larger vesicles or remnant membranes. This result was consistent with the biochemical data and with gold localization of $GM_1$ performed on cells (Parton, R. G., *J. Histochem. Cytochem.* 42:155 (1994); Montesano, R., et al., *Nature* 296:651 (1982)). Control experiments performed with conjugates plus a 10-fold molar excess of monomeric cholera toxin showed almost complete absence of gold.

Although several previous studies that have examined the immunolocalization of GPI-anchored proteins in cultured cells concluded that these proteins reside in caveolae (Rothberg, K. G., et al., *J. Cell. Biol.* 110:637 (1990); Ying, Y., et al., *Cold Spring Harbor Symp. Quant. Biol.* 57:593 (1992); Ryan, U. S., et al., *J. Appl. Physiol.* 53:914 (1982); Stahl, A. and Mueller, B. M., *J. Cell Biol.* 129:335 (1995)) reexamination of the published electron micrographs reveals little gold labeling directly inside the caveolae. Almost all of this labeling is actually adjacent to the caveolae on the flat plasma membrane directly attached to, but not a part of, the neck of the caveolae. The small amount of labeling apparent inside the caveolae and the extent of clustering observed may be induced artifactually by antibody cross-linking (Mayor, S., et al., *Science* 264:1948 (1994)). The data provided herein confirm that GPI-anchored proteins are not within the caveolae, but are attached to membrane that is adjacent to the caveolae.

This is not meant to imply that GPI-anchored proteins can never enter the caveolae. Antibody-cross-linked alkaline phosphatase clusters and slowly enters caveolae for endocytosis to endosomes and lysosomes (Parton, R. G., et al., *J. Cell Biol.* 127:1199 (1994)), consistent with studies of internalization of modified albumins by caveolae, with the exception that the process of binding, clustering, internalization, and degradation was much quicker to the albumin (Oh, P., et al., *J. Cell Biol.* 127:1217 (1994); Schnitzer, J. E., et al., *J. Biol. Chem.* 264:24544 (1992); Schnitzer, J. E. and Bravo, J., *J. Biol. Chem.* 268:7562 (1993)). It appears that cell surface processing, at least for GPI-linked proteins, probably comprises three distinct sequential steps: (i) induced movement of GPI-anchored proteins (probably by a ligand) into microdomains near the caveolae, thereby increasing the local concentration of GPI-linked proteins by direct sequestration of previously free molecules or possibly by assembly of several small clusters; (ii) eventual movement into the caveolae; and (iii) fission or budding of the caveolae from the membrane for photocytosis or endocytosis.

EQUIVALENTS

Those skilled in the art will recognize or be able to ascertain using no more than routine experimentation, many equivalents to the specific embodiments described herein. Such equivalents are intended to be encompassed in the scope of the claims.

What is claimed is:

1. A method of delivering an agent of interest to a luminal surface of vascular endothelium in a tissue-specific manner, comprising the steps of:

a) selecting an agent of interest that binds to and localizes to a component of a microdomain of the luminal surface of the vascular endothelium upon contact with the luminal surface, wherein the component of the micromain to which the agent binds and localizes is tissue specific, and wherein the microdomain is selected from the group consisting of: caveolae, G domains, and caveolae associated with G domains; and b) contacting the luminal surface of vasculature with the agent of interest, thereby delivering the agent to the luminal surface of the vascular endothelium in a tissue-specific manner.

2. The method of claim 1, wherein the tissue is malignant.

3. The method of claim 1, wherein the agent of interest comprises a nucleic acid.

4. The method of claim 1, wherein the agent of interest comprises an immunotoxin.

5. The method of claim 1, wherein the agent of interest comprises an active agent component and a transport agent component, wherein the transport agent component binds to and localizes to a component of the microdomain of the luminal surface of the vascular endothelium.

6. The method of claim 5, wherein the active agent component is selected from the group consisting of: an antibody, a nucleic acid, a drug, a toxin, and a diagnostic agent.

7. The method of claim 5, wherein the transport agent component binds to and localizes to a molecule present on the luminal surface of a microdomain of the luminal surface of the vascular endothelium.

8. The method of claim 5, wherein the active agent component and the transport agent component are the same component.

9. The method of claim 8, wherein the active agent component is selected from the group consisting of: an antibody, a drug, a toxin, and a diagnostic agent.

10. The method of claim 5, wherein the transport agent component is selected from the group consisting of: an antibody, a peptide, an inactivated virus, a receptor, a ligand and a nucleic acid.

11. The method of claim 10, wherein the transport agent component is an antibody.

12. The method of claim 1, wherein the tissue is selected from the group consisting of: vascular, pulmonary, cardiac, cerebral, nephric, hepatic, endocrinous and intestinal tissue.

13. The method of claim 12, wherein the vascular endothelium of a tissue is vascular endothelium of cardiac tissue, and wherein the agent of interest comprises a selective stimulant.

14. The method of claim 12, wherein the vascular endothelium of a tissue is vascular endothelium of a blood vessel, and wherein the agent of interest comprises an anticoagulant.

* * * * *